United States Patent
Geslin et al.

(10) Patent No.: US 6,806,282 B2
(45) Date of Patent: Oct. 19, 2004

(54) BRANCHED SUBSTITUTED AMINO DERIVATIVES OF 3-AMINO-1-PHENYL-1H-[1,2,4]TRIAZOL, METHODS FOR PRODUCING THEM AND PHARMACEUTICAL COMPOSITIONS CONTAINING THEM

(75) Inventors: Michel Geslin, Villeneuve Tolosane (FR); Danielle Gully, Muret (FR); Jean-Pierre Maffrand, Portet sur Garonne (FR); Pierre Roger, Montigny le Bretonneux (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/149,499
(22) PCT Filed: Dec. 14, 2000
(86) PCT No.: PCT/FR00/03536
§ 371 (c)(1),
(2), (4) Date: Jun. 12, 2002
(87) PCT Pub. No.: WO01/44207
PCT Pub. Date: Jun. 21, 2001

(65) Prior Publication Data
US 2003/0162771 A1 Aug. 28, 2003

(30) Foreign Application Priority Data
Dec. 17, 1999 (FR) .......................................... 99 15935

(51) Int. Cl.$^7$ .................. A61K 31/4196; C07D 249/14
(52) U.S. Cl. ..................................... 514/383; 548/264.8
(58) Field of Search ........................ 548/264.8; 514/383

(56) References Cited

U.S. PATENT DOCUMENTS 4,925,864 A * 5/1990 Inamori et al.

FOREIGN PATENT DOCUMENTS

| WO | WO 96/39400 | 12/1996 |
| WO | WO 98/51686 | 11/1998 |

OTHER PUBLICATIONS

Trinka, Peter et al., J. Heterocycl. Chem., (1995) vol. 32, No. 4, pp. 1359–1371.

Derwent Patent Abstract No. 199906.

* cited by examiner

*Primary Examiner*—Taofiq Solola
(74) *Attorney, Agent, or Firm*—Michael D. Alexander; Paul E. Dupont

(57) ABSTRACT

The present invention relates to novel branched substituted amino derivatives of 3-amino-1-phenyl-1H-[1,2,4]triazole, processes for their preparation and pharmaceutical compositions comprising them.

20 Claims, No Drawings

BRANCHED SUBSTITUTED AMINO DERIVATIVES OF 3-AMINO-1-PHENYL-1H-[1,2,4]TRIAZOL, METHODS FOR PRODUCING THEM AND PHARMACEUTICAL COMPOSITIONS CONTAINING THEM

This application is a 371 of PCT/FR00/03536 filed Dec. 14, 2000.

A subject-matter of the present invention is novel branched substituted amino derivatives of 3-amino-1-phenyl-1H-[1,2,4]triazole, processes for their preparation and the pharmaceutical compositions comprising them.

These novel triazole derivatives have an antagonistic activity with respect to CRF (corticotropin releasing factor) and can thus constitute active principles of pharmaceutical compositions.

Corticotropin releasing factor (CRF) is a peptide whose sequence of 41 amino acids was characterized by Vale W. et al. in 1981 (Science, 1981, 213, 1394–1397). CRF is the main endogenous factor involved in the regulation of the hypothalamohypophysosuprarenal axis (release of adrenocorticotropic hormone: ACTH) and its pathologies, and also in the depressive syndromes which result from its dysfunctioning. CRF also causes the secretion of β-endorphin, of β-lipotropin and of corticosterone. CRF is therefore the physiological regulator of the secretion of adrenocorticotropic hormone (ACTH) and of cortisol by the effect of ACTH at the suprarenal level and more generally of peptides derived from proopiomelanocortin (POMC). In addition to its location in the hypothalamus, CRF is widely distributed in the central nervous system but also in extraneuronal tissues, such as the suprarenal glands and the testicles. The presence of CRF has also been demonstrated during inflammatory processes.

Numerous animal experiments have shown that the central administration of CRF causes varied anxiogenic effects, such as modification of the behaviour in general: for example neophobia, reduction in sexual receptivity and decrease in food consumption and slow-wave sleep in the rat. The intracerebroventricular injection of CRF also increases the excitation of the noradrenergic neurons of the locus coeruleus which is often associated in animals with a state of anxiety. In the rat, the central or peripheral administration of CRF or of related peptides (for example urocortin, sauvagine) induces, in addition to central effects, such as increase in alertness and in emotional reactivity to the surroundings, modifications in gastric dumping, in acid secretion, in intestinal transit time and in faecal excretion, as well as tensional effects. CRF is also involved in the complex regulation of inflammatory responses, on the one hand with a pro-inflammatory role in some animal models (degranulation of mastocytes resulting in the release of inflammatory molecules, such as histamine, prostaglandins, and the like) and, on the other hand, as inhibitor of the effects brought about by the increase in the vascular permeability as a result of the inflammation.

The use of a peptide antagonist, α-helical CRF(9-41) (αH-CRF), or of specific antibodies (Rivier J. et al., Science, 1984, 224, 889–891) has made it possible to confirm the role of this peptide in all these effects. These experiments have also confirmed the important role of CRF in man in the integration of the complex responses observed during physiological, psychological or immunological stress, simultaneously at the neuroendocrinal, visceral and behavioural levels (Morley J. E. et al., Endocrine Review, 1987, 8, 3, 256–287; Smith M. A. et al., Horm. Res., 1989, 31, 66–71). In addition, clinical data militate in favour of the effective involvement of CRF in many disorders resulting from a condition of stress (Gulley L. R. et al., J. Clin. Psychiatry, 1993, 54, 1, (suppl.), 16–19), for example:

the existence of the CRF test (i.v. administration) in man has made it possible to show the modification in the ACTH response in depressive patients (Breier A. et al., Am. J. Psychiatry, 1987, 144, 1419–1425).

the discovery of an endogenous CRF hypersecretion in certain pathologies, for example a high level of CRF in the cephalorrhachidian fluid in non-medicated patients who are depressed or affected by dementia of Alzheimer's disease type (Nemeroff C. B. et al., Science 1984, 226, 4680, 1342–1343; Regul. Pept., 1989, 25, 123–130) or a decreased density of CRF receptors in the cortex of suicide victims (Nemeroff C. B. et al., Arch. Gen. Psychiatry, 1988, 45, 577–579).

the dysfunctioning of CRF-dependent neurons is even suggested in the severe pathologies which are Alzheimer's and Parkinson's diseases, Huntington's chorea and amyotrophic lateral sclerosis (De Souza E. B., Hospital Practice, 1988, 23, 59).

The central administration of CRF in many animal species produces behavioural effects similar to those obtained in man in stress situations. When they are repeated over time, these effects can result in various pathologies, such as: fatigue, hypertension, heart and tensional disorders, modification in gastric dumping and in faecal excretion (colitis, irritable bowel), modification in acid secretion, hyperglycaemia, retarded growth, anorexia, neophobia, migraines, reproductive disorders, immunosuppression (inflammatory processes, multiple infections and cancers) and varied neuropsychiatric disorders (depression, anorexia or bulimia nervosa and anxiety).

The injection via the intracerebroventricular route of the reference peptide antagonist, αH-CRF (9-41), prevents the effects obtained either by the administration of exogenous CRF or by the use of stress-inducing agents (ether, restraint, noise, electric shock, weaning from ethanol or surgery) capable by themselves of inducing an increase in the level of endogenous CRF. These results are confirmed by the study of many antagonist peptide molecules which are structurally related to CRF and which have a prolonged duration of action with respect to αH-CRF (9-41) (Rivier J. et al., J. Med. Chem., 1993, 36, 2851–2859; Menzaghi F. et al., J. Pharmacol. Exp. Ther., 1994, 269, 2, 564–572; Hernandez J. F. et al., J. Med. Chem., 1993, 36, 2860–2867).

Such CRF-antagonist peptide compounds are disclosed, for example, in U.S. Pat. No. 5,109,111, U.S. Pat. No. 5,132,111 and U.S. Pat. No. 5,245,009 and in patent applications WO 92/22 576 and WO 96/19 499.

In addition, preliminary studies have shown that tricyclic anti-depressants can modulate the level of CRF and the number of rCRF receptors in the brain (Grigoriadis D. E. et al., Neuropsychopharmacology, 1989, 2, 53–60). Likewise, benzodiazepine anxiolytics are capable of inhibiting the effect of CRF (Britton K. T. et al., Psychopharmacology, 1988, 94, 306), without the mechanism of action of these substances being entirely elucidated. These results confirm, if necessary, the growing need for non-peptide antagonist molecules for CRF receptors.

It is also important to point out three possible consequences of conditions of chronic stress, which are immunodepression, fertility disorders and the development of diabetes.

CRF exerts such effects by interacting with specific membrane receptors which have been characterized in the pituitary gland and the brain of numerous species (mouse, rat and man), as well as in the heart, the squelettal muscle (rat, mouse) and in the myometrium and the placenta during pregnancy.

The 3-amino-1-phenyl-1H-[1,2,4]triazole compounds are not represented to any great extent. Mention may be made in particular of compounds carrying a phenyl at the 5-position as disclosed by Ebenreth A. et al. (Pharmazie, 1992, 47(7), 556–7) and by Bozo E., Szilagil G. and Janaky J. (Arch. Pharm., 1989, 322(10), 583–7, Patents Nos. HU44522, HU195791, 1986), who claim antiinflammatory-antirheumatic properties. In two Japanese patents (JP 02091061 and JP 2729810, 1988), Inamori et al. claim the preparation of 3-amino-1-phenyl-1H-[1,2,4]triazoles as insecticides.

In the Neurocrine patent application published under the number WO 96/39 400, 3-amino-5-phenyl-1H-[1,2,4] triazole compounds are disclosed as antagonists of CRF receptors.

It has now been found, according to the present invention, that some 3-amino-1-phenyl-1H-[1,2,4]triazole derivatives which are a subject-matter of the present invention have an excellent affinity with respect to CRF receptors. Furthermore, due to their structure, these molecules have good dispersibility and/or solubility in solvents or solutions commonly used in therapeutics, which confers a pharmacological activity on them and also make possible the ready preparation of oral and parenteral pharmaceutical dosage forms.

A subject-matter of the present invention is the compounds, in the racemic or enantiomeric form, of formula:

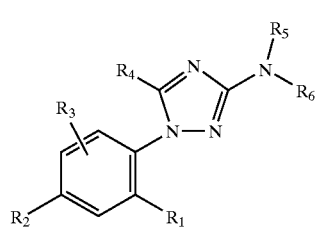

(I)

in which:
$R_1$ and $R_2$ represent, each independently of the other, a halogen atom; a $(C_1-C_5)$alkyl; a $(C_1-C_5)$alkoxy; a nitro, trifluoromethyl or cyano group; an $NR_aR_b$ amino group in which $R_a$ and $R_b$ represent, each independently of the other, a hydrogen, a $(C_1-C_3)$alkyl or a $CO(C_1-C_3)$alkyl or else in which $R_a$ and $R_b$ constitute, with the nitrogen atom to which they are bonded, a 5- to 7-membered heterocycle; or an S—R group in which R represents a hydrogen atom or a $(C_1-C_5)$alkyl, it being possible for the sulphur atom to be monooxidized or dioxidized;

$R_3$ represents hydrogen or is as defined above for $R_1$;

$R_4$ represents hydrogen; a halogen; a $(C_1-C_5)$alkyl; a $(C_3-C_5)$cycloalkyl; a $(C_3-C_5)$cycloalkyl$(C_1-C_2)$alkyl; or an $R_c$—X—$(C_1-C_2)$alkyl group in which $R_c$ represents hydrogen or a $(C_1-C_3)$alkyl and X represents O, S, SO or $SO_2$;

$R_5$ represents a $(C_1-C_5)$alkyl, an alkynyl with 3 to 5 carbon atoms or an alkenyl with 3 to 5 carbon atoms; a $(C_3-C_5)$cycloalkyl$(C_1-C_3)$alkyl; or a $(C_1-C_3)$alkyl-X—$(C_0-C_3)$alkyl in which X represents O, S, SO or $SO_2$;

$R_6$ represents a phenyl group substituted by one or more Z radicals, at least one of which is in the 2-position, and Z represents a halogen; a nitro, trifluoromethyl or cyano group; a $(C_1-C_5)$alkyl; a $(C_1-C_5)$alkyl-X— or $(C_1-C_3)$alkyl-X—$(C_1-C_2)$alkyl in which X represents O, S, SO or $SO_2$; a hydroxy$(C_1-C_3)$alkyl; or a $COR_d$ or $COOR_d$ where $R_d$ represents a $(C_1-C_3)$alkyl or a $(C_3-C_5)$cycloalkyl;

or else $R_6$ represents —$CHR_7R_8$, in which $R_7$ represents a $(C_3-C_5)$ cycloalkyl; a phenyl group which can be substituted in the 3-, 4- and 5-positions by one or more Z' radicals, with Z' representing a halogen; a nitro, trifluoromethyl or cyano group; a $(C_1-C_5)$alkyl; a $(C_1-C_5)$alkyl-X— or $(C_1-C_3)$alkyl-X—$(C_1-C_2)$alkyl where X represents O, S, SO or $SO_2$; a hydroxy$(C_1-C_3)$ alkyl; a $COR_d$ or $COOR_d$ in which $R_d$ is as defined above; a methylenedioxy or an ethylenedioxy; or else a pyridyl group optionally substituted by an $NR_aR_b$ amino group as defined above or by a Z' radical as defined above;

$R_8$ represents a $(C_1-C_6)$alkyl; a $(C_3-C_5)$cycloalkyl; a $(C_3-C_5)$ cycloalkyl$(C_1-C_3)$alkyl; a $(C_1-C_3)$alkyl-X—$(C_1-C_3)$alkyl where X represents O, S, SO or $SO_2$; or a $(C_3-C_5)$ cycloalkyl $(C_1-C_2)$alkyl-X—$(C_1-C_3)$alkyl where X represents O, S, SO or $SO_2$;

and their pharmaceutically acceptable addition salts, their hydrates and/or their solvates.

In the present description, the term "halogen" is understood to mean a fluorine, chlorine, bromine or iodine atom. The alkyl groups or the alkoxy groups are linear or branched.

According to another of its aspects, the invention relates to the compounds of formula (I), in the racemic or enantiomeric form, in which:
$R_1$ and $R_2$ represent, each independently of the other, a halogen atom; a $(C_1-C_5)$alkyl; a $(C_1-C_5)$alkoxy; a trifluoromethyl or an S—R group in which R represents a $(C_1-C_5)$alkyl;

$R_3$ represents hydrogen or a $(C_1-C_5)$alkyl;

$R_4$ represents a $(C_1-C_5)$alkyl; a $(C_3-C_5)$cycloalkyl or an $R_a$—X—$(C_1-C_2)$alkyl group in which $R_a$ represents a $(C_1-C_3)$alkyl and X represents O;

$R_5$ represents a $(C_1-C_5)$alkyl or an alkynyl with 3 to 5 carbon atoms;

$R_6$ represents —$CHR_7R_8$, in which $R_7$ represents a phenyl group which can be substituted in the 3-, 4- and 5-positions by one or more Z' radicals, with Z' representing a halogen; a $(C_1-C_5)$alkyl; a $(C_1-C_5)$alkyl-X— or $(C_1-C_3)$alkyl-X—$(C_1-C_2)$alkyl where X represents O; or a methylenedioxy group;

$R_8$ represents a $(C_1-C_6)$alkyl; a $(C_3-C_5)$cycloalkyl $(C_1-C_3)$alkyl; or a $(C_1-C_3)$alkyl-X—$(C_1-C_3)$alkyl where X represents O;

and their pharmaceutically acceptable addition salts, their hydrates and/or their solvates.

According to another of its aspects, the invention relates to the compounds of formula (I), in the racemic or enantiomeric form, in which $R_5$ represents a propyl or propargyl group and to their pharmaceutically acceptable addition salts, to their hydrates and/or to their solvates.

The invention relates more particularly to the above compounds in the enantiomeric form.

According to another of its aspects, the invention relates to the following compounds:

5-Cyclopropyl-N-[2-cyclopropyl-1-(4-fluorophenyl) ethyl]-1-(2,4-dichlorophenyl)-N-propyl-1H-1,2,4-triazol-3-amine hydrochloride (Example 7)

N-[2-Cyclopropyl-1-(4-fluorophenyl)ethyl]-1-(2,4-dichlorophenyl)-5-(methoxymethyl)-N-propyl-1H-1,2,4-triazol-3-amine hydrochloride (Example 9)

N-[2-Cyclopropyl-1-(4-fluorophenyl)ethyl]-1-[2,6-dichloro-4-(trifluoromethyl)phenyl]-5-methyl-N-propyl-1H-1,2,4-triazol-3-amine hydrochloride (Example 10)

1-(2-Chloro-4-methoxy-5-methylphenyl)-N-[2-cyclopropyl-1-(4-fluorophenyl)ethyl]-5-methyl-N-(2-propynyl)-1H-1,2,4-triazol-3-amine hydrochloride (Example 13)

1-(2-Chloro-4-methoxy-5-methylphenyl)-N-[2-cyclopropyl-1-(4-fluorophenyl)ethyl]-5-methyl-N-propyl-1H-1,2,4-triazol-3-amine hydrochloride (Example 14)

1-(2-Chloro-4-methoxy-5-methylphenyl)-5-cyclopropyl-N-[2-cyclopropyl-1-(4-fluorophenyl)ethyl]-N-(2-propynyl)-1H-1,2,4-triazol-3-amine hydrochloride (Example 15)

5-Cyclopropyl-N-[2-cyclopropyl-1-(4-fluorophenyl)ethyl]-1-[2,6-dichloro-4-(trifluoromethyl)phenyl]-N-propyl-1H-1,2,4-triazol-3-amine hydrobromide (Example 18)

5-Cyclopropyl-N-(2-cyclopropyl-1-phenylethyl)-1-(2,4-dichlorophenyl)-N-propyl-1H-1,2,4-triazol-3-amine hydrochloride (Example 19)

1-(2-Chloro-4-methoxy-5-methylphenyl)-5-cyclopropyl-N-(2-cyclopropyl-1-phenylethyl)-N-propyl-1H-1,2,4-triazol-3-amine hydrochloride (Example 20)

1-(2-Chloro-4-methoxy-5-methylphenyl)-5-cyclopropyl-N-[(1S)-2-cyclopropyl-1-(3-fluoro-4-methylphenyl)ethyl]-N-propyl-1H-1,2,4-triazol-3-amine hydrochloride (Example 22)

1-(2-Chloro-4-methoxy-5-methylphenyl)-5-cyclopropyl-N-(2-cyclopropyl-1-phenylethyl)-N-(2-propynyl)-1H-1,2,4-triazol-3-amine hydrochloride (Example 23)

1-(2-Chloro-4-methoxy-5-methylphenyl)-5-cyclopropyl-N-[(1R)-1-(4-fluorophenyl)-2-methoxyethyl]-N-propyl-1H-1,2,4-triazol-3-amine hydrochloride (Example 24)

1-(2-Chloro-4-methoxy-5-methylphenyl)-5-cyclopropyl-N-[(1S)-2-cyclopropyl-1-(3-fluoro-4-methylphenyl)ethyl]-N-(2-propynyl)-1H-1,2,4-triazol-3-amine hydrobromide (Example 25)

5-Cyclopropyl-N-[2-cyclopropyl-1-(3-fluoro-4-methylphenyl)ethyl]-1(2,4-dichlorophenyl)-N-propyl-1H-1,2,4-triazol-3-amine hydrochloride (Example 26)

5-Cyclopropyl-1-(2,4-dichlorophenyl)-N-[(1R)-1-(4-fluorophenyl)-2-methoxyethyl]-N-propyl-1H-1,2,4-triazol-3-amine hydrochloride (Example 27)

5-Cyclopropyl-N-[(1S)-2-cyclopropyl-1-(3-fluoro-4-methylphenyl)ethyl]-1-(2,4-dimethylphenyl)-N-propyl-1H-1,2,4-triazol-3-amine hydrochloride (Example 28)

1-(2,4-Dichlorophenyl)-5-ethyl-N-[(1S)-1-phenylbutyl]-N-propyl-1H-1,2,4-triazol-3-amine hydrochloride (Example 29)

1-(2-Chloro-4-methoxy-5-methylphenyl)-5-methyl-N-[(1S)-1-phenylbutyl]-N-propyl-1H-1,2,4-triazol-3-amine hydrochloride (Example 30)

1-(2-Chloro-4-methoxy-5-methylphenyl)-N-[(1S)-2-cyclopropyl-1-(3-fluoro-4-methylphenyl)ethyl]-5-methyl-N-propyl-1H-1,2,4-triazol-3-amine hydrochloride (Example 31)

N-[(1S)-2-Cyclopropyl-1-(4-fluorophenyl)ethyl]-1-(2,4-dichlorophenyl)-5-methyl-N-propyl-1H-1,2,4-triazol-3-amine hydrochloride (Example 32)

1-(2-Chloro-4-methoxy-5-methylphenyl)-N-[(1S)-2-cyclopropyl-1-(3-fluoro-4-methylphenyl)ethyl]-5-ethyl-N-propyl-1H-1,2,4-triazol-3-amine hydrochloride (Example 33)

N-[(1S)-2-Cyclopropyl-1-(4-fluorophenyl)ethyl]-1-(2,4-dichlorophenyl)-5-ethyl-N-propyl-1H-1,2,4-triazol-3-amine hydrochloride (Example 34)

1-(2-Chloro-4-methoxy-5-methylphenyl)-N-[(1S)-2-cyclopropyl-1-(3-fluoro-4-methylphenyl)ethyl]-5-methyl-N-(2-propynyl)-1H-1,2,4-triazol-3-amine hydrochloride (Example 35)

5-Cyclopropyl-1-(2,4-dichlorophenyl)-N-[(1S)-1-phenylbutyl]-N-propyl-1H-1,2,4-triazol-3-amine hydrochloride (Example 36)

1-(2-Chloro-4-methoxy-5-methylphenyl)-N-[(1S)-2-cyclopropyl-1-(4-fluorophenyl)ethyl]-5-ethyl-N-propyl-1H-1,2,4-triazol-3-amine hydrochloride (Example 37)

N-[(1S)-2-Cyclopropyl-1-(3-fluoro-4-methylphenyl)ethyl]-1-(2,4-dichlorophenyl)-5-methyl-N-propyl-1H-1,2,4-triazol-3-amine hydrochloride (Example 38)

1-(2-Chloro-4-methoxy-5-methylphenyl)-N-[(1S)-2-cyclopropyl-1-(4-methylphenyl)ethyl]-5-methyl-N-propyl-1H-1,2,4-triazol-3-amine hydrochloride (Example 39)

N-[(1S) -2-Cyclopropyl-1-(4-methylphenyl)ethyl]-1-(2,4-dichlorophenyl)-5-methyl-N-propyl-1H-1,2,4-triazol-3-amine hydrochloride (Example 40)

1-(2-Chloro-4-methoxy-5-methylphenyl)-5-cyclopropyl-N-[(1S)-1-phenylbutyl]-N-propyl-1H-1,2,4-triazol-3-amine hydrochloride (Example 41)

1-(2-Chloro-4-methoxy-5-methylphenyl)-N-[(1S)-2-cyclopropyl-1-(4-fluorophenyl)ethyl]-5-methyl-N-propyl-1H-1,2,4-triazol-3-amine hydrochloride (Example 42)

1-[2-Chloro-4-(trifluoromethyl)phenyl]-N-[(1S)-2-cyclopropyl-1-(3-fluoro-4-methylphenyl)ethyl]-5-methyl-N-propyl-1H-1,2,4-triazol-3-amine hydrochloride (Example 43)

N-[(1S) -1-(1,3-Benzodioxol-5-yl)-2-cyclopropylethyl]-1-(2-chloro-4-methoxy-5-methylphenyl)-5-methyl-N-propyl-1H-1,2,4-triazol-3-amine hydrochloride (Example 44)

N-[(1S)-1-(1,3-Benzodioxol-5-yl)-2-cyclopropylethyl]-1-(2,4-dichlorophenyl)-5-methyl-N-propyl-1H-1,2,4-triazol-3-amine hydrochloride (Example 45)

1-(2-Chloro-4-methoxy-5-methylphenyl)-N-{(1S) -2-cyclopropyl-1-[(4-methoxymethyl)phenyl]ethyl}-5-methyl-N-propyl-1H-1,2,4-triazol-3-amine hydrochloride (Example 46)

1-(2-Chloro-4-methoxyphenyl)-N-[(1S)-2-cyclopropyl-1-(3-fluoro-4-methylphenyl)ethyl]-5-methyl-N- propyl-1H-1,2,4-triazol-3-amine hydrochloride (Example 47)

1-(2-Chloro-4-methoxy-5-methylphenyl)-N-(1S)-2-cyclopropyl-1-phenyl)ethyl]-5-methyl-N-propyl-1H-1,2,4-triazol-3-amine hydrochloride (Example 48)

N-[(1S)-2-Cyclopropyl-1-phenyl)ethyl]-1-(2,4-dichlorophenyl)-5-methyl-N-propyl-1H-1,2,4-triazol-3-amine hydrochloride (Example 49)

1-(2-Chloro-4-methoxy-5-methylphenyl)-5-cyclopropyl-N-[(1S)-1-(4-methylphenyl)butyl]-N-propyl-1H-1,2,4-triazol-3-amine hydrochloride (Example 50)

5-Cyclopropyl-1-(2,4-dichlorophenyl)-N-[(1S)-1-(4-methylphenyl)butyl]-N-propyl-1H-1,2,4-triazol-3-amine hydrochloride (Example 51)

1-[2-Chloro-4-(methylsulphanyl)phenyl]-N-[2-cyclopropyl-1-(3-fluoro-4-methylphenyl)ethyl]-5-methyl-N-propyl-1H-1,2,4-triazol-3-amine hydrochloride (Example 52)

1-(2-Chloro-4-methoxyphenyl)-N-[(1S)-2-cyclopropyl-1-(4-fluorophenyl)ethyl]-5-methyl-N-propyl-1H-1,2,4-triazol-3-amine hydrochloride (Example 53)

to the corresponding bases, to the other pharmaceutically acceptable addition salts, to their solvates and/or to their hydrates.

The compounds of the invention in the free form generally exhibit weak base properties.

The salts of the compounds of formula (I) with pharmaceutically acceptable acids are the preferred salts but those which can make it possible to isolate the compounds of formula (I), in particular to purify them or to obtain pure enantiomers or diastereoisomers, are also a subject-matter of the invention.

Mention may be made, among the pharmaceutically acceptable acids for the preparation of the addition salts to the compounds of formula (I), of hydrochloric, hydrobromic, phosphoric, fumaric, citric, oxalic, sulphuric, ascorbic, tartaric, maleic, mandelic, methanesulphonic, lactobionic, gluconic, glucaric, succinic, sulphonic or hydroxypropane-sulphonic acids.

The compounds of the invention can be prepared according to two synthetic routes A and B.

Synthetic route A is represented in SCHEME 1.

SCHEME 1: Route A

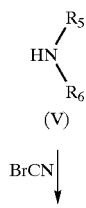

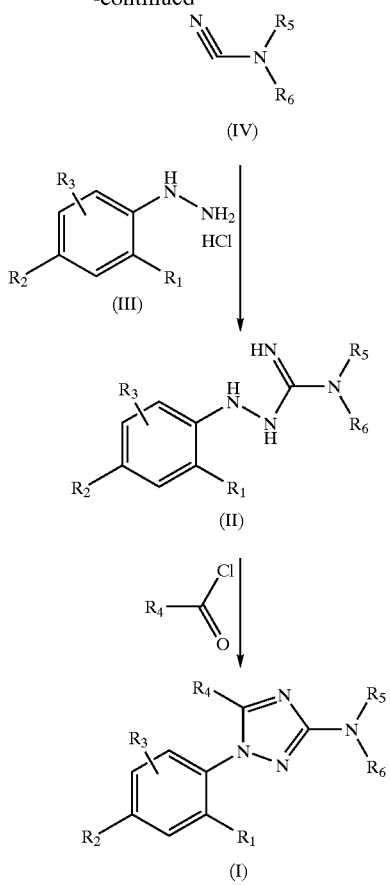

By route A, the compound (I) is prepared by condensation of the anilinoguanidine hydrochloride (II) with an acid halide of $R_4$—CO—X type or an acid anhydride $R_4$—CO—O—CO—$R_4$ in the presence of an organic base (pyridine, triethylamine, and the like) in an organic solvent, preferably pyridine.

In the case where $R_4$ represents hydrogen, the acid halide is replaced by formic acid (Chem. Ber., 1965, 98, 1476–1486).

The anilinoguanidine hydrochloride (II) is obtained by reaction of a phenylhydrazine hydrochloride (III) with a cyanamide (IV) in a refluxing alcohol, preferably isopropanol, according to the method described by Erczi et al. (Eur. J. Med. Chem., 1993, 28, 185–193).

The phenylhydrazine hydrochloride (III) may be commercially available or may be prepared from the corresponding aniline by diazotization and then reduction by tin(II) chloride or by alkaline sulphates.

The cyanamide (IV) is prepared from the secondary amine (V) by reaction with cyanogen bromide in an organic solvent, such as diethyl ether or acetonitrile.

This synthetic route A is particularly efficient when $R_5$ is a group of alkyl type.

Synthetic route B is represented in SCHEME 2.

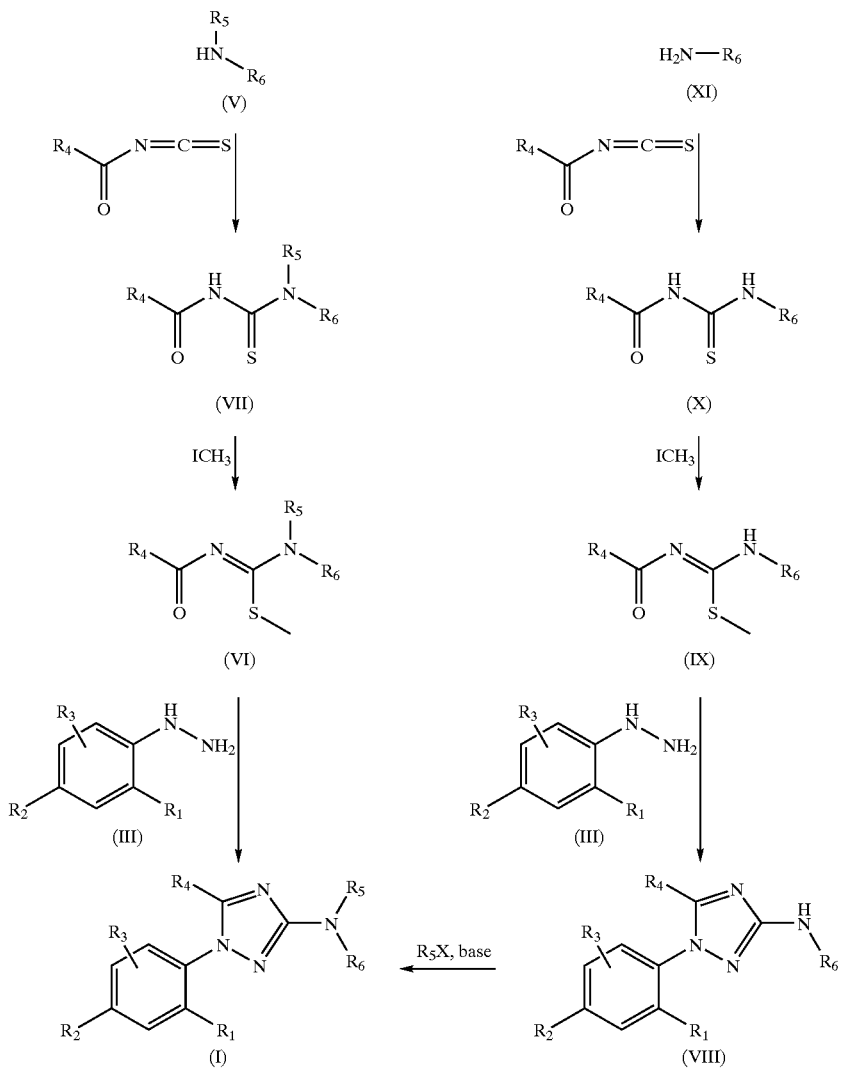

When the starting amine is secondary, the alternative form B1 is used and when it is primary, the alternative form B2 is used.

By route B1, the aminotriazole (I) is prepared by condensation of phenylhydrazine (III) with an N-acyl-S-methylisothiourea (VI) by heating in toluene, xylene, dimethylformamide or dimethyl sulphoxide. When the phenylhydrazine (III) is salified, for example in the hydrochloride form, a base such as triethylamine, N,N-diethylaniline or caesium carbonate is added.

The N-acyl-S-methylisothiourea (VI) is obtained from the N-acylthiourea (VII) by S-methylation with iodomethane in a solvent, such as dichloromethane or tetrahydrofuran, after the action of a base, preferably sodium hydride, or else in dimethylformamide or tetrahydrofuran in the presence of caesium carbonate.

The N-acylthiourea (VII) is obtained by addition of the secondary amine (V) to the acyl isothiocyanate $R_4CONCS$. The operating conditions, temperature and solvent can vary according to the reactivity of the amines. The solvents used can be, for example, acetone, dichloromethane, benzene, toluene or chloroform.

The acyl isothiocyanate $R_4CONCS$ is prepared beforehand by reaction between an acyl halide $R_4COCl$ and an alkaline thiocyanate (ammonium thiocyanate, for example) in acetone, generally.

By route B2, the aminotriazole (I) is prepared from an NH aminotriazole (VIII) by an alkylation reaction. The operating conditions vary according to the reactivity of the secondary amine and of the halide. The systems used can be: sodium hydride/DMF, potassium hydride/benzene/crown ether, potassium hydride/tetrahydrofuran/crown ether, alkaline tert-butoxide/DMSO.

The synthetic conditions for the preparation of the NH aminotriazole (VIII) from the primary amine (XI) via the intermediates N-alcylthiourea (X) and then N-acyl-S-methylisothiourea (IX) are similar to those described for route B1.

The compounds of formula (I) are salified, generally in the hydrochloride form. These hydrochlorides can be in the form of crystalline or amorphous solids obtained by precipitation from a solvent (or a mixture of solvents), such as pentane, diisopropyl ether or diethyl ether.

The primary amines (XI) and the secondary amines (V) used, when they exhibit an asymmetric carbon ($R_6$=CH($R_8$) $R_7$), can be in the racemic or enantiomeric form.

Among the usual methods for the synthesis of primary amines, two methods have been particularly used, one from amino acid, the other from substituted phenyl ketone (1). In the latter case, the synthesis is carried out according to SCHEME 3 below. The substituted phenyl ketone (1) is converted to the oxime (2) and then to the benzyloxime (3). The benzyloxime (3) is reduced, either with lithium aluminium hydride, in order to obtain a racemic amine, or with a chiral complex, such as a chiral oxazaborolidine-borane complex, in order to obtain an amine in the form of an enantiomer.

SCHEME 3

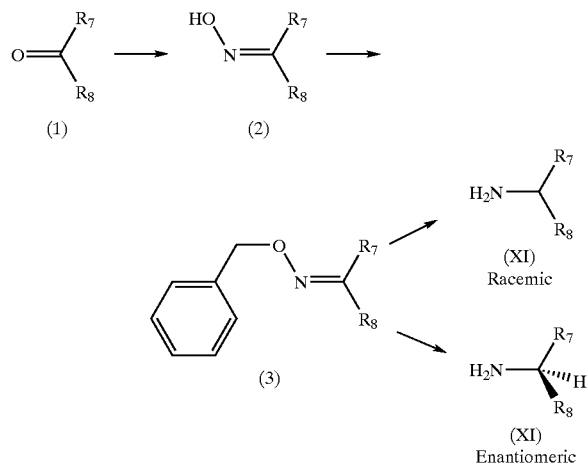

The compounds of formula (I) above also comprise those in which one or more hydrogen or carbon atoms have been replaced by their radioactive isotope, for example tritium or carbon-14. Such labelled compounds are of use in research, metabolic or pharmacokinetic work or alternatively in biochemical assays as receptor ligands.

The compounds of the present invention have formed the subject of biochemical and pharmacological studies. They have highly advantageous pharmacological properties. The compounds of the invention displace, at concentrations of less than 10 µM, the binding of iodinated CRF or related peptides (urotensin, sauvagine), for example $^{125}$I-Tyr-CRF, to receptors present on brain membranes or on cultured cells, according to the method described by E. B. De Souza (J. Neurosci., 1987, 7, 1, 88–100).

The antagonist activity of the compounds according to the invention has been demonstrated by their ability to inhibit some activities associated with CRF. In particular, the compounds of formula (I) are capable of inhibiting the secretion of corticotropin (ACTH) induced by CRF. The study on the secretion of ACTH induced by CRF has been carried out in vivo in conscious rats, according to a method adapted from C. Rivier et al., Endocrinology, 1982, 110(1), 272–278.

CRF is a neuropeptide which controls the activity of the hypothalamohypophysosuprarenal axis. This factor is responsible for endocrinal and behavioural responses related to stress.

Indeed, it has been shown that CRF can modulate the behaviour and also some functions of the autonomous nervous system (G. F. Koob, F. E. Bloom, Fed. Proc., 1985, 44, 259; M. R. Brown, L. A. Fisher, Fed. Proc., 1985, 44, 243). More particularly, CRF induces the secretion of corticotropin (ACTH), β-endorphins and other peptides derived from proopiomelanocortin (A. Tazi et al., Regul. Peptides, 1987, 18, 37; M. R. Brown et al., Regul. Peptides, 1986, 16, 321; C. L. Williams et al., Am. J. Physiol., 1987, G 582, 253).

The compounds of the invention may therefore be used in regulating the secretion of these endogenous substances. They are more especially applied as active principles in medicaments for decreasing the response to stress (behaviour, emotional states, gastrointestinal and cardiovascular disorders or disorders of the immune system) and more generally in pathologies involving CRF, for example psychiatric disorders, anxiety, depression, anorexia and bulimia nervosa, epilepsy, disorders of sexual activity and of fertility, Alzheimer's disease or others.

The compounds of the invention are very stable and are therefore particularly appropriate in forming the active principle of medicaments.

The invention also applies to the pharmaceutical compositions comprising, as active principle, a compound of formula (I) or one of its pharmaceutically acceptable salts, optionally in combination with one or more appropriate inert excipients.

In each dosage unit, the active principle of formula (I) is present in amounts suitable for the daily doses envisaged. Each dosage unit is suitably adjusted according to the dosage and the type of administration anticipated, for example tablets, hard gelatin capsules and the like, chartulas, phials, syrups and the like, drops or transdermal or transmucosal patches, so that such a dosage unit comprises 0.5 to 800 mg of active principle, preferably 0.5 to 200 mg having to be administered each day.

The compounds according to the invention can also be used in combination with another active principle used in the desired therapy, such as, for example, anxiolytics, antidepressants or anorexigenics.

The compounds of formula (I) have little toxicity; their toxicity is compatible with their use as a medicament in the treatment of the above disorders and diseases.

The compounds of formula (I) can be formulated in pharmaceutical compositions for administration to mammals, in particular man, for the treatment of the above-said diseases.

The pharmaceutical compositions thus obtained are advantageously presented in various forms, such as, for example, injectable solutions or solutions to be taken orally, dragees, tablets or hard gelatin capsules. Pharmaceutical compositions comprising at least one compound of formula (I) or one of its salts as active principle are in particular of use in the preventive or curative treatment of diseases related to stress and more generally in the treatment of all pathologies involving CRF, such as, for example: Cushing's disease, neuropsychiatric disorders, such as depression, anxiety, panic attacks, post-traumatic stress, compulsive obsessive disorders, mood disorders, behavioural disorders, aggressiveness, anorexia, bulimia, hyperglycaemia, premature labour, at-risk pregnancies, retarded growth, sleep disorders, epilepsy and depressions of all types; degenerative disorders: Alzheimer's or Parkinson's disease; Huntington's chorea and amyotrophic lateral sclerosis; vascular, cardiac and cerebral disorders; disorders of sexual activity and of fertility; premature labour, immunodepression, immunosuppression, inflammatory processes, multiple infections, interstitial cystitis, rheumatoid arthritis, osteoarthritis, uveitides, psoriasis and diabetes; cancers; functional gastrointestinal disorders and inflammations which result therefrom (irritable and inflammatory colon, diarrhoea); disorders of pain perception, fibromyalgias related or not related to sleep disorders, fatigue or migraine; or symptoms related to (alcohol) dependence and to weaning from drugs.

The posology can vary widely as a function of the age, weight and state of health of the patient, of the nature and severity of the ailment and of the administration route. This posology comprises the administration of one or more doses of approximately 0.5 mg to 800 mg of active principle, preferably 0.5 to 200 mg, each day.

In the pharmaceutical compositions of the present invention for oral, sublingual, subcutaneous, intramuscular, intravenous, transdermal, transmucosal, local or rectal administration, the active principle can be administered to animals and human beings in unit forms of administration, mixed with conventional pharmaceutical vehicles. Appropriate unit forms of administration comprise forms intended for the oral route, such as tablets, hard gelatin capsules, powders, granules and solutions or suspensions to be taken orally, forms for sublingual and buccal administration, forms for subcutaneous, intramuscular, intravenous, intranasal or intraocular administration and forms for rectal administration.

The following EXAMPLES, given without implied limitation, illustrate the invention.

The methods for the synthesis of the various intermediates which make it possible to obtain the compounds of the invention are described in the PREPARATIONS. These intermediates are all obtained according to methods well known to a person skilled in the art.

The melting points were measured according to the Micro-Köfler technique and are expressed in degrees Celsius.

The proton nuclear magnetic resonance ($^1$H NMR) spectra were recorded in deuterated chloroform ($CDCl_3$), unless otherwise mentioned, at 200 MHz or at 300 MHz. The chemical shapes are expressed in ppm and the coupling constants in Hertz.

The enantiomeric excesses (ee) are evaluated from the chromatograms obtained either by chiral phase HPLC chromatography or by chiral supercritical fluid chromatography (SFC).

The optical rotations of the optical active products are characterized by their $[\alpha]^\circ_D$ (the concentrations c of the solutions analysed are expressed in grams per 100 ml).

The abbreviations used below are as follows: S=singulet; m=multiplet; d=doublet; t=triplet; q=quartet; c-Pr= cyclopropyl radical; Ph=phenyl radical.

The compounds of the invention exhibit an elemental analysis in accordance with theory.

The compounds of the invention described in TABLES 1 and 6 also have NMR spectra and mass spectra in accordance with their structures.

PREPARATION OF THE STARTING SYNTHONS

1) Preparation of the Phenylhydrazines of Formula III

2-Chloro-4-methoxy-5-methylphenylhydrazine hydrochloride Compound III.1

A solution of 8.6 g (50 mmol) of 2-chloro-4-methoxy-5-methylaniline in 75 ml of 5N hydrochloric acid is stirred at −5° C. and 3.52 g (51 mmol) of sodium nitrite, in solution in 12.5 ml of water, are added. The mixture is stirred for one hour at 0° C. and then a solution of 22.56 g (100 mmol) of tin(II) chloride dihydrate in 20 ml of 35% hydrochloric acid is added. The mixture is stirred for two hours with gradual return to ambient temperature. The precipitate formed is filtered off and washed with normal hydrochloric acid, ethanol and diethyl ether. After drying in a desiccator, 7.8 g of compound III.1 are obtained. M.p.=140° C. Yield 70%.

$^1$H NMR ($d_6$-DMSO, δ ppm): 2.09 (s, 3H, $CH_3$); 3.73 (s, 3H, $OCH_3$); 7.0 (s, 1H, Ph); 7.05 (s, 1H, Ph); 7.58 (s, 1H, NH); 10.13 (s, 3H, $NH_3^+$)

2) Preparation of the Secondary Amines of Formula V

[2-Cyclopropyl-1-(4-fluorophenyl)ethyl]propylamine Compound V.1

A solution of 8.9 g (50 mmol) of 2-cyclopropyl-1-(4-fluorophenyl)ethanone in 100 ml of dichloromethane with 16.4 ml (200 mmol) of propylamine is stirred at 0° C. and 30 ml of a normal solution of titanium tetrachloride in dichloromethane are slowly added. The mixture is stirred for 15 hours at ambient temperature and then cooled to 0° C., and 100 ml of methanol are added. 2.1 g (55 mmol) of sodium borohydride are added portionwise and the mixture is stirred for two hours at ambient temperature. The mixture is concentrated under reduced pressure to approximately 100 ml and then 100 ml of water are added. The suspension is filtered and the filtrate, taken up in dichloromethane, is washed with water and then with water saturated with sodium chloride and dried over sodium sulphate and then the solvents are evaporated under reduced pressure. 9.43 g of oily product are obtained. Yield 85%.

$^1$H NMR ($CDCl_3$, δ ppm): −0.08–0.12 (m, 2H, c-Pr); 0.28–0.50 (m, 2H, c-Pr); 0.50–0.62 (m, 1H, c-Pr); 0.81–0.88 (m, 3H, $CH_3$); 1.35–1.70 (m, 5H, $CH_2$, $CH_2$-c-Pr and NH); 2.30–2.45 (m, 2H, N—$CH_2$); 3.62–3.68 (m, 1H, CH); 6.90–7.05 (m, 2H, Ph); 7.21–7.31 (m, 2H, Ph).

3) Preparation of the Primary Amines of Formula XI

First Method: Preparation of the Primary Amines from Amino Acids a) (1R)-2-amino-2-(4-fluorophenyl)ethanol 240 ml (240 mmol) of a 1M solution of lithium aluminium hydride in tetrahydrofuran are stirred at reflux and then 20 g (118 mmol) of (R)-(4-fluorophenyl)glycine are added portionwise. After stirring at reflux for six hours and 30 minutes, the reaction mixture is stirred at 0° C. and then 9.5 ml of water, 9.5 ml of a 15% sodium hydroxide solution and then 28.5 ml of water are slowly added. The suspension obtained is filtered through celite. The filtrate is concentrated and taken up in 1 liter of dichloromethane. The solution is washed with a saturated sodium chloride solution and dried over anhydrous sodium sulphate and then the solvents are evaporated under reduced pressure. Crystallization from isopropyl ether makes it possible to obtain 13.22 g (85.2 mmol) of crystalline product. Yield 72%. M.p.=95° C.

$^1$H NMR ($d_6$-DMSO): 1.82 (s, 2H, $NH_2$); 3.35–3.45 (m, 2H, $CH_2O$); 3.84 (m, 1H, CH); 4.73 (s, 1H, OH); 7.01–7.13 (m, 2H, Ph); 7.30–7.41 (m, 2H, Ph).

b) (1R)-1-(4-Fluorophenyl)-2-methoxyethylamine Compound XI.1

3.64 g (91 mmol) of potassium hydride, obtained by washing 8.1 g of an oily suspension with pentane, are suspended in 70 ml of tetrahydrofuran and stirred at 10° C. A solution of 13.22 g (85 mmol) of (1R)-2-amino-2-(4-fluorophenyl)ethanol in 175 ml of tetrahydrofuran is slowly added. After stirring for 16 hours at ambient temperature, a solution of 5.2 ml (83.5 mmol) of iodomethane in 105 ml of tetrahydrofuran is added over 2 hours. The reaction mixture is stirred for 3 hours at ambient temperature and is then poured onto 1 liter of ice-cold salt water. The mixture is extracted with 1 liter of tert-butyl methyl ether. The organic phase is washed with water and then with a saturated sodium chloride solution and dried over anhydrous sodium sulphate and then the solvents are evaporated under reduced pressure. 11.87 g (70 mmol) of oily amine are obtained. Yield 82%.

$^1$H NMR (CDCl$_3$): 1.66 (s, 2H, NH$_2$); 3.29 (d, 1H, CH$_2$) 3.36 (s, 3H, OCH$_3$); 3.45 (dd, 1H, CH$_2$); 4.16 (m, 1H, CH); 6.93–7.05 (m, 2H, Ph); 7.24–7.38 (m, 2H, Ph).

Second Method: Preparation of the Primary Amines from Phenyl Ketones a) Synthesis of Substituted Phenyl Ketones Compound 1

Procedure A

2-Cyclopropyl-1-(3-fluoro-4-methylphenyl)ethan-1-one Compound 1.1

A solution of 61 g (323 mmol) of 4-bromo-3-fluorotoluene in 280 ml of diethyl ether is slowly added to 7.8 g (323 mmol) of magnesium turnings, so as to bring about a gentle reflux. The mixture is subsequently heated at reflux for two hours and then cooled and filtered through glass wool. The filtrate is stirred at 0° C. and 25 g (308 mmol) of cyclopropylacetonitrile, diluted in 20 ml of diethyl ether, are added. The reaction mixture is stirred for three hours at ambient temperature and is then cooled to 0° C., and a 1N hydrochloric acid solution is slowly added until a pH of 1 is obtained. The mixture is extracted three times with ethyl acetate and the combined organic phases are washed with water and then with water saturated with sodium chloride and dried over sodium sulphate, the solvents are evaporated under reduced pressure. 53 g of crude product are obtained, which product is used as is in the following stage. Yield: approximately 85%.

$^1$H NMR (CDCl$_3$, δ ppm): 0.15–0.21 (m, 2H, c-Pr); 0.55–0.65 (m, 2H, c-Pr); 1.07–1.20 (m, 1H, c-Pr); 2.31 (d, J=1.9 Hz, 3H, CH$_3$); 2.82 (d, J=6.7 Hz, 2H, CH$_2$-c-Pr); 7.22–7.30 (m, 1H, Ph); 7.54–7.64 (m, 2H, Ph).

The following ketone was synthesized by the same process:

2-Cyclopropyl-1-(4-methylphenyl)ethan-1-one Compound 1.2

Procedure B

2-Cyclopropyl-1-(4-methoxymethylphenyl)ethan-1-one Compound 1.3

A solution of 32.5 g (162 mmol) of 1-bromo-4-methoxymethylphenyl in 300 ml of tetrahydrofuran is stirred at −60° C. and 112 ml (179 mmol) of a 1.6M butyllithium solution are slowly added. The reaction mixture is stirred for 30 minutes at −60° C. and then a solution of 27.6 g (192 mmol) of 2-cyclopropyl-N-methoxy-N-methylacetamide is slowly added. The reaction mixture is stirred while allowing the temperature to gradually return to ambient temperature. After stirring for 4 hours, it is cooled to 0° C. and 5 ml of ethanol are slowly added. The mixture is extracted with ethyl acetate and the organic phase is washed with water and then with a saturated sodium chloride solution and dried over anhydrous sodium sulphate, and then the solvents are evaporated under reduced pressure. The residue obtained is purified by chromatography on a column of silica gel (solvent: cyclohexane then 20/1 (v/v) cyclohexane/ethyl acetate). 21.8 g of ketone are obtained. Yield 66%.

$^1$H NMR (CDCl$_3$, δ ppm): 0.13–0.21 (m, 2H, c-Pr); 0.53–0.62 (m, 2H, c-Pr); 0.84–0.93 (m, 1H, c-Pr); 2.85 (d, J=6.6 Hz, 2H, CH$_2$-c-Pr); 3.40 (s, 3H, OCH$_3$); 4.68 (s, 2H, OCH$_2$); 7.57 (d, J=7.5 Hz, 2H, Ph); 7.92 (d, J=7.5 Hz, 2H, Ph).

The following ketone was synthesized by the same process:

2-Cyclopropyl-1-(3,4-methylenedioxyphenyl)ethan-1-one Compound 1.4 b) Synthesis of Substituted Oximes Compound 2

(E)-2-Cyclopropyl-1-(3-fluoro-4-methylphenyl)ethan-1-one oxime Compound 2.1

A solution of 53 g (275 mmol) of compound 1.1 in 200 ml of pyridine is stirred at 0° C. and 28.5 g (410 mmol) of hydroxylamine hydrochloride are slowly added. The mixture is stirred for 12 hours at ambient temperature and is then concentrated under reduced pressure. The residue is taken up in ethyl acetate and the organic phase is washed three times with water and then with water saturated with sodium chloride and dried over sodium sulphate, and then the solvents are evaporated under reduced pressure. The residue is purified by chromatography on a column of silica gel (eluent: 20/1 (v/v) cyclohexane/ethyl acetate). 30 g of oxime are obtained. Yield 52%.

$^1$H NMR (d$_6$-DMSO, δ ppm): 0.10–0.20 (m, 2H, c-Pr); 0.28–0.40 (m, 2H, c-Pr); 0.78–0.95 (m, 1H, c-Pr); 2.21 (d, J=1.7 Hz, 3H, CH$_3$); 2.63 (d, J=6.8 Hz, 2H, CH$_2$-c-Pr); 7.20–7.56 (m, 3H, Ph); 11.16 (s, 1H, OH).

The following oximes were synthesized by the same process:

2-cyclopropyl-1-phenylethan-1-one (E)-oxime Compound 2.2
2-cyclopropyl-1-(4-fluorophenyl)ethan-1-one (E)-oxime Compound 2.3
2-cyclopropyl-1-(4-methylphenyl)ethan-1-one (E)-oxime Compound 2.4
2-cyclopropyl-1-(4-methoxymethylphenyl)ethan-1-one (E)-oxime Compound 2.5
2-cyclopropyl-1-(3,4-methylenedioxyphenyl)ethan-1-one (E)-oxime Compound 2.6
1-phenylbutan-1-one (E)-oxime Compound 2.7
1-(4-methylphenyl)butan-1-one (E)-oxime Compound 2.8 c) Synthesis of Substituted O-benzyloximes Compound 3

2-Cyclopropyl-1-(3-fluoro-4-methylphenyl)ethan-1-one (E)-O-benzyloxime Compound 3.1

A solution of 30 g (144 mmol) of compound 2.1 in 140 ml of dimethylformamide is stirred at 0° C. and 8.3 g (180 mmol) of 55% sodium hydride in oil are added portionwise. The mixture is stirred for 30 minutes at 0° C. and then 20.5 ml (172 mmol) of benzyl bromide are slowly added. The reaction mixture is stirred for three hours at ambient temperature and is then cooled to 0° C., and 10 ml of ethanol and then 500 ml of water are added. The mixture is extracted with ethyl acetate and the organic phase is washed with water and then with water saturated with sodium chloride and dried over sodium sulphate, and the solvents are evaporated under reduced pressure. The residue is purified by chromatography on a column of silica gel (eluent: 95/5 (v/v)

cyclohexane/dichloromethane). 30.2 g of E-benzyloxime are obtained. Yield 70%.

$^1$H NMR (d$_6$-DMSO, δ ppm): 0.10–0.17 (m, 2H, c-Pr); 0.28–0.40 (m, 2H, c-Pr); 0.78–0.90 (m, 1H, c-Pr); 2.22 (d, J=1.8 Hz, 3H, CH$_3$); 2.67 (d, J=6.8 Hz, 2H, CH$_2$-c-Pr); 5.16 (s, 2H, O—CH$_2$—Ph); 7.20–7.43 (m, 8H, Ph).

The following benzyloximes were synthesized by the same process:

2-Cyclopropyl-1-phenylethan-1-one (E)-O-benzyloxime Compound 3.2

2-Cyclopropyl-1-(4-fluorophenyl)ethan-1-one (E)-O-benzyloxime Compound 3.3

2-Cyclopropyl-1-(4-methylphenyl)ethan-1-one (E)-O-benzyloxime Compound 3.4

2-Cyclopropyl-1-(4-methoxymethylphenyl)ethan-1-one (E)-O-benzyloxime Compound 3.5

2-Cyclopropyl-1-(3,4-methylenedioxyphenyl)ethan-1-one (E)-O-benzyloxime Compound 3.6

1-Phenylbutan-1-one (E)-O-benzyloxime Compound 3.7

1-(4-Methylphenyl)butan-1-one (E)-O-benzyloxime Compound 3.8 d) Synthesis of Racemic Primary Amines of Formula XI

2-Cyclopropyl-1-(4-fluorophenyl)ethylamine Compound XI.2

A suspension of 10.6 g (280 mmol) of lithium aluminium hydride in 500 ml of tetrahydrofuran is stirred at ambient temperature and 40 g (140 mmol) of 2-cyclopropyl-1-(4-fluorophenyl)ethan-1-one O-benzyloxime are slowly added. The mixture is stirred at reflux for four hours and is then cooled to 0° C., and 10.6 ml of water, 10.6 ml of a 15% sodium hydroxide solution and then 32 ml of water are added dropwise. The suspension obtained is filtered through celite and washed with ethyl acetate. The combined organic filtrates are washed with water and then with water saturated with sodium chloride and dried over sodium sulphate, and the solvents are evaporated under reduced pressure. The crude extract is purified by chromatography on a column of silica gel (eluent: 95/5 (v/v) dichloromethane/methanol). 14.2 g of amine are obtained in the oily form. Yield 57%.

$^1$H NMR (CDCl$_3$, δ ppm): –0.05–0.18 (m, 2H, c-Pr); 0.32–0.50 (m, 2H, c-Pr); 0.50–0.70 (m, 1H, c-Pr); 1.40–1.70 (m, 2H, CH$_2$-c-Pr); 1.76 (s, 2H, NH$_2$); 3.97–4.05 (m, 1H, CH); 6.92–7.04 (m, 2H, Ph); 7.24–7.34 (m, 2H, Ph).

The following racemic amines were synthesized by the same process:

2-Cyclopropyl-1-phenylethylamine Compound XI.3

2-Cyclopropyl-1-(3-fluoro-4-methylphenyl) ethylamine Compound XI.4 e) Synthesis of Chiral Primary Amines of Formula XI (1S)-2-Cyclopropyl-1-(3-fluoro-4-methylphenyl) ethylamine Compound XI.5

A solution of 37.17 g (145 mmol) of (S)-2-amino-3-methyl-1,1-diphenylbutan-1-ol in 180 ml of tetrahydrofuran is stirred at –40° C. and 285 ml of a 1M solution of borane-tetrahydrofuran complex (285 mmol) are slowly added. The mixture is stirred for three hours from –40° C. to ambient temperature and is then cooled to –10° C., and a solution of 17 g (57 mmol) of compound 3.1 is added. The reaction mixture is stirred for twenty hours at ambient temperature and is then cooled to –10° C., and 285 ml of 2N hydrochloric acid are added. The mixture is left to stir for twenty hours and then the tetrahydrofuran is evaporated under reduced pressure. An (S)-2-amino-3-methyl-1,1-diphenylbutan-1-ol hydrochloride precipitate is formed and is filtered off and rinsed with 1N hydrochloric acid. The combined acidic filtrates are washed with tert-butyl methyl ether, then cooled to 0° C. and basified slowly with a 35% aqueous sodium hydroxide solution. After extracting three times with dichloromethane, the combined organic phases are washed with water and then with water saturated with sodium chloride and dried over sodium sulphate, and the solvents are evaporated under reduced pressure. The residue is purified by chromatography on a column of silica gel (eluent: 95/5 (v/v) dichloromethane/methanol). 7.2 g of amine are obtained in oily form. Yield 47%. ee>98%.

$[\alpha]_D^{22}$=+5.4 (c=1.16, dichloromethane) $^1$H NMR (CDCl$_3$, δ ppm): –0.05–0.15 (m, 2H, c-Pr); 0.35–0.50 (m, 2H, c-Pr); 0.55–0.70 (m, 1H, c-Pr); 1.43–1.70 (m, 2H, CH$_2$-c-Pr); 2.0 (s, 2H, NH$_2$); 2.25 (d, J=1.7 Hz, 3H, CH$_3$); 3.99–4.04 (m, 1H, CH); 6.99–7.17 (m, 3H, Ph).

The following chiral amines were synthesized by the same process:

(1S)-2-Cyclopropyl-1-phenylethylamine ee=96% Compound XI.6

(1S)-2-Cyclopropyl-1-(4-fluorophenyl)ethylamine ee=98% Compound XI.7

(1S)-2-Cyclopropyl-1-(4-methylphenyl)ethylamine ee=97.2% Compound XI.8

(1S)-2-Cyclopropyl-1-(4-methoxymethylphenyl)-ethylamine ee=97.8% Compound XI.9

(1S)-2-Cyclopropyl-1-(3,4-methylenedioxyphenyl)-ethylamine ee=96.6% Compound XI.10

(1S)-1-Phenylbutylamine ee>99% Compound XI.11

(1S)-1-(4-Methylphenyl)butylamine ee=97.9% Compound XI.12

The enantiomeric excesses (ee) of these compounds were evaluated by chiral supercritical fluid chromatography of their acetamide or thiourea derivative. Only the enantiomeric excess of compound XI.11 was evaluated directly by chiral phase HPLC. For this compound, salification and then recrystallization with N-acetyl-L-leucine (Yamamoto Y. et al., Bull. Chem. Soc. Jpn., 1976, 49(11), 3247–3249) made it possible to improve the enantiomeric excess.

Preparation by Route A

1) Preparation of the Cyanamides of Formula IV (1-Phenylbutyl)propylcyanamide Compound IV.1

A suspension of 1.4 g (16.4 mmol) of magnesium carbonate in 20 ml of a 9/1 (v/v) diethyl ether/water mixture is stirred at 0° C. and 5 g (47 mmol) of cyanogen bromide are added. 9 g (47 mmol) of (1-phenylbutyl)propylamine are added slowly to this mixture, stirred at 0° C. After stirring for one hour at ambient temperature, 50 ml of water and then 100 ml of diethyl ether are added to the reaction mixture.

The ethereal phase is washed with water and then with a saturated sodium chloride solution. It is dried over sodium sulphate and then the solvents are evaporated under reduced pressure. The oily residue obtained is distilled in a bulb oven at 150° C. under ≅0.3 mm of Hg. 7.6 g of colourless oil are obtained. Yield 74%.

$^1$H NMR (CDCl$_3$, δ ppm): 0.84–0.95 (m, 6H, 2CH$_3$); 1.28–2.10 (m, 6H, 3CH$_2$); 2.65–2.90 (m, 2H, NCH$_2$); 3.77 (t, J=7.5 Hz, 1H, CH); 7.25–7.39 (m, 5H, Ph).

The following compound was synthesized by the same method:

[2-Cyclopropyl-1-(4-fluorophenyl)ethyl]propylcyanamide Compound IV. 2

$^1$H NMR (CDCl$_3$, δ ppm): 0–0.2 (m, 2H, c-Pr); 0.37–0.55 (m, 2H, c-Pr); 0.60–0.75 (m, 1H, c-Pr); 0.85–0.93 (m, 3H, CH$_3$); 1.55–1.75 (m, 3H, CH$_2$ and HC$\underline{H}$-c-Pr); 1.95–2.10 (m, 1H, HC$\underline{H}$-c-Pr); 2.72–2.90 (m, 2H, NCH$_2$); 3.87 (t, J=7.5 Hz, 1H, CH); 6.98–7.09 (m, 2H, Ph); 7.25–7.35 (m, 2H, Ph).

2) Preparation of the Anilinoguanidines of Formula II

N-(2,4-Dichlorophenylamino)-N'-(1-phenylbutyl)-N'-propylguanidine hydrochloride Compound II.1

A mixture composed of 5.13 g (24 mmol) of 2,4-dichlorophenylhydrazine hydrochloride, 6.5 g (30 mmol) of compound IV.1 and 10 ml of anhydrous n-propanol is stirred at 130° C. for twenty-four hours. After having been cooled, the reaction mixture is suspended in 50 ml of diethyl ether. The precipitate is filtered off and then taken up in 50 ml of acetone. The suspension obtained is stirred for 30 minutes at ambient temperature and then the precipitate is filtered off and washed with acetone. It is subsequently dissolved under warm conditions in 10 ml of methanol and then 50 ml of diethyl ether are added. A white precipitate is formed and is filtered off, washed with ether and dried. 6 g (14 mmol) of white powder are obtained. Yield 58%. M.p.=225° C.

The following compound was synthesized by the same method:

N-[2-Cyclopropyl-1-(4-fluorophenyl)ethyl]-N'-(2,4-dichlorophenylamino)-N-propylguanidine hydrochloride Compound II.2

$^1$H NMR (d$_6$-DMSO, δ ppm): 0.1–0.7 (m, 5H, c-Pr); 0.78 (m, 3H, CH$_3$); 1.4–1.75 (m, 2H, CH$_2$); 1.85–2.15 (m, 2H, CH$_2$); 3.0–3.4 (m, 2H, NCH$_2$); 5.41 (t, 7.3 Hz, 1H, CH); 7.73 (d, 1H, Ph); 7.1–7.6 (m, 6H, Ph); 8.1 (s, 2H, NH$_2$); 8.23 (s, 1H, NH); 9.98 (s, 1H, NH).

3) Preparation of the Aminotriazoles of Formula I by Route A

EXAMPLE 1

[1-(2,4-Dichlorophenyl)-5-methyl-N-(1-phenylbutyl)-N-propyl-1H-1,2,4-triazol-3-amine A suspension of 1.29 g (3 mmol) of compound 11.1 in 12 ml of pyridine is stirred at 0° C. and 1.07 ml (15 mmol) of acetyl chloride are slowly added. The reaction mixture is stirred for 20 hours at ambient temperature and is then poured onto 100 ml of ice-cold water. After acidifying to pH 1 with 1N hydrochloric acid, the mixture is extracted with ethyl acetate. The organic phase is subsequently washed with a saturated sodium hydrogencarbonate solution, with water and then with water saturated with sodium chloride. It is dried with anhydrous sodium sulphate and then evaporated. The crude residue is purified by chromatography on a column of silica gel (eluent: 9/1 (v/v) cyclohexane/ethyl acetate). 645 mg (1.54 mmol) of colourless gummy product are obtained. Yield 52%.

$^1$H NNR CDCl$_3$, δ ppm): 0.71 (m, 3H, CH$_3$); 0.94 (m, 3H, CH$_3$); 1.35–1.55 (m, 4H, 2CH$_2$); 1.96–2.02 (m, 2H, CH$_2$); 2.23 (s, 3H, CH$_3$); 2.97–3.07 (m, 2H, NCH$_2$); 5.41 (t, J=7.6 Hz, 1H, CH); 7.18–7.40 (m, 7H, Ph); 7.53 (d, J=1.9 Hz, 1H, Ph).

This product is salified in the hydrochloride form; M.p.= 1.42° C. (HCl).

Examples 2 to 9 in the Following TABLE 1 are Synthesized by the Same Method

TABLE 1

Compounds of formula I synthesized by Route A (I)

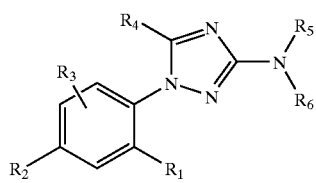

| Example No. | R$_1$, R$_2$, R$_3$ | R$_4$ | R$_5$ | R$_6$ | Salt; M.p. (° C.) |
|---|---|---|---|---|---|
| 2 | 2-Cl 4-Cl H | 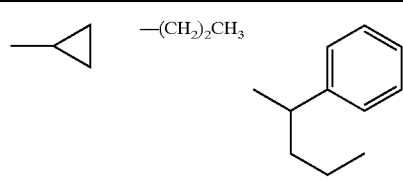 | —(CH$_2$)$_2$CH$_3$ |  | HCl; 114 |

TABLE 1-continued

Compounds of formula I synthesized by Route A (I)

| Example No. | $R_1, R_2, R_3$ | $R_4$ | $R_5$ | $R_6$ | Salt; M.p. (° C.) |
|---|---|---|---|---|---|
| 3 | 2-Cl 4-Cl H | —CH$_3$ | —(CH$_2$)$_2$CH$_3$ | 1-(4-fluorophenyl)-2-cyclopropyl-ethyl (with methyl branch) | HCl; 142 |
| 4 | 2-Cl 4-Cl H | —CH$_2$CH$_3$ | —(CH$_2$)$_2$CH$_3$ | 1-(4-fluorophenyl)-2-cyclopropyl-ethyl | HCl; 153 |
| 5 | 2-Cl 4-Cl H | —CH$_2$CH$_2$CH$_3$ | —(CH$_2$)$_2$CH$_3$ | 1-(4-fluorophenyl)-2-cyclopropyl-ethyl | HCl; 141 |
| 6 | 2-Cl 4-Cl H | isopropyl (CH$_3$, CH$_3$) | —(CH$_2$)$_2$CH$_3$ | 1-(4-fluorophenyl)-2-cyclopropyl-ethyl | HCl; 153 |
| 7 | 2-Cl 4-Cl H | cyclopropyl | —(CH$_2$)$_2$CH$_3$ | 1-(4-fluorophenyl)-2-cyclopropyl-ethyl | HCl; 132 |
| 8 | 2-Cl 4-Cl H | cyclobutyl | —(CH$_2$)$_2$CH$_3$ | 1-(4-fluorophenyl)-2-cyclopropyl-ethyl | HCl; 144 |

TABLE 1-continued

Compounds of formula I synthesized by Route A

(I)

| Example No. | $R_1, R_2, R_3$ | $R_4$ | $R_5$ | $R_6$ | Salt; M.p. (° C.) |
|---|---|---|---|---|---|
| 9 | 2-Cl 4-Cl H | —CH$_2$OCH$_3$ | —(CH$_2$)$_2$CH$_3$ | 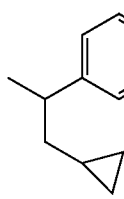 | HCl; 130 |

Preparation by Route B1

1) Preparation of the N-acylthioureas of Formula VII

N-acetyl-N'-[2-cyclopropyl-1-(4-fluorophenyl)ethyl]-N'-propylthiourea Compound VII.1

A solution of 2 g (26.4 mmol) of ammonium thiocyanate in 27 ml of acetone is stirred at ambient temperature and 1.82 ml (24.2 mmol) of acetyl chloride are slowly added. After stirring for 10 minutes, a solution of 4.87 g (22 mmol) of compound V.1 in 44 ml of dichloromethane is slowly added. After stirring for 30 minutes at ambient temperature, 100 ml of dichloromethane and 100 ml of water are added to the reaction mixture. The organic phase is washed with water and then with water saturated with sodium chloride and dried over sodium sulphate, and the solvents are evaporated under reduced pressure. The crude residue is purified by chromatography on a column of silica gel (eluent: 4/1 (v/v) cyclohexane/ethyl acetate). 5.5 g (17 mmol) of compound VII.1 are obtained. Yield 77%.

$^1$H NMR (d$_6$-DMSO, δ ppm): 0.1–0.2 (m, 2H, c-Pr); 0.35–0.50 (m, 2H, c-Pr); 0.50–0.70 (m, 3H, CH$_3$); 0.75–0.95 (m, 1H, c-Pr); 1.25–1.75 (m, 2H, CH$_2$); 1.80–2.10 (m, 5H, CH$_2$-c-Pr and COCH$_3$); 3.10–3.60 (m, 2H, NCH$_2$); 5.32 (m, 1H, CH); 7.15–7.24 (m, 2H, Ph); 7.55–7.62 (m, 2H, Ph); 10.33 (s, 1H, NH).

2) Preparation of N-acyl-S-methylisothioureas of Formula VI

N-acetyl-N'-[2-cyclopropyl-1-(4-fluorophenyl)ethyl]-S-methyl-N'-propylisothiourea Compound VI.1

A solution of 5.5 g (17 mmol) of compound VII.1 in 170 ml of dichloromethane is stirred at 0° C. and 740 mg (18.5 mmol) of 60% sodium hydride in oil are added. After stirring for 10 minutes at 0° C., 2.1 ml (34 mmol) of methyl iodide are added to the reaction mixture. The reaction mixture is stirred for three hours at ambient temperature and is then cooled to 0° C., and 10 ml of ethanol and then 10 ml of water are added. The organic phase is washed with water and then with water saturated with sodium chloride, dried over sodium sulphate then and the solvents are evaporated under reduced pressure. The colourless and oily crude residue is used as is in the following stage (quantitative yield).

$^1$H NMR (CDCl$_3$, δ ppm): 0.1–0.16 (m, 2H, c-Pr); 0.45–0.52 (m, 2H, c-Pr); 0.62–0.70 (m, 3H, CH$_3$); 0.80–0.95 (m, 1H, CH, c-Pr); 1.0–1.2 and 1.45–1.65 (2m, 2H, CH$_2$); 1.8–2.05 (m, 2H, CH$_2$-c-Pr); 2.18 (s, 3H, CH$_3$CO); 2.41 (s, 3H, SCH$_3$); 3.04–3.20 (m, 2H, NCH$_2$); 5.80 (t, 7.6 Hz, 1H, CH); 6.96–7.08 (m, 2H, Ph); 7.30–7.38 (m, 2H, Ph).

3) Preparation of the Aminotriazoles of Formula (I) by Route B1

EXAMPLE 10

N-[2-Cyclopropyl-1-(4-fluorophenyl)ethyl]-1-[2,6-dichloro-4-(trifluoromethyl)phenyl]-5-methyl-N-propyl-1H-1,2,4-triazol-3-amine A mixture composed of 1 g (3 mmol) of compound VI.1, 1 g (4 mmol) of 2,6-dichloro-4-trifluoromethylphenylhydrazine and 8 ml of anhydrous dimethyl sulphoxide is stirred and gradually heated from 100 to 200° C. over thirty hours until the starting isothiourea has disappeared. The reaction mixture, cooled beforehand, is poured into ice-cold water and acidified with normal hydrochloric acid. The mixture is extracted with ethyl acetate and the organic extract is washed with a saturated aqueous sodium hydrogencarbonate solution, then with water and with water saturated with sodium chloride. It is dried over anhydrous sodium sulphate then and the solvents are evaporated under reduced pressure. The crude residue is purified on a column of silica gel (eluent: 9/1 (v/v) cyclohexane/methyl acetate). 690 mg of gummy product are obtained. Yield 44%.

$^1$H NMR (CDCl$_3$, δ ppm): 0.08–0.18 (m, 2H, c-Pr); 0.37–0.41 (m, 2H, c-Pr); 0.67–0.75 (m, 3H, CH$_3$ and 1H, c-Pr); 1.30–1.45 and 1.50–1.65 (2m, 2H, CH$_2$); 1.84–2.03 (m, 2H, CH$_2$-c-Pr); 2.21 (s, 3H, CH$_3$); 2.94–3.02 and 3.10–3.18 (2m, 2H, NCH$_2$); 5.43 (t, 7.5 Hz, 1H, CH); 6.93–7.0 (m, 2H, Ph); 7.36–7.41 (m, 2H, Ph); 7.71 (s, 2H, Ph).

The compound is salified in the hydrochloride form; M.p.=135° C. (HCl).

Preparation by Route B2
1) Preparation of the N-acylthioureas of Formula X

N-acetyl-N'-[2-cyclopropyl-1-(4-fluorophenyl)-ethyl]thiourea Compound X.1

A solution of 3.38 g (44.4 mmol) of ammonium thiocyanate in 44 ml of acetone is stirred at ambient temperature and 3.07 ml (40.7 mmol) of acetyl chloride are added. After stirring for 5 minutes, 88 ml of benzene are added and the reaction mixture is heated to 60° C. A solution of 6.62 g (37 mmol) of compound XI.2 in 27 ml of benzene is then added. The temperature is maintained at 60° C. for 5 minutes and then the mixture is cooled to ambient temperature and diluted with 100 ml of ethyl acetate. The mixture is washed with water and then with water saturated with sodium chloride and dried over sodium sulphate, and the solvents are evaporated under reduced pressure. The crude residue (11 g) is purified by chromatography on a column of silica gel (eluent: 4/1 (v/v) cyclohexane/ethyl acetate). 5.6 g of compound X.1 are obtained. Yield 54%.

$^1$H NMR (CDCl$_3$, δ ppm): 0.10–0.25 (m, 2H, c-Pr); 0.45–0.60 (m, 2H, c-Pr); 0.60–0.75 (m, 1H, c-Pr); 1.75–1.85 (m, 2H, CH$_2$-c-Pr); 2.11 (s, 3H, CH$_3$CO); 5.38–5.49 (m, 1H, CH); 6.95–7.06 (m, 2H, Ph); 7.22–7.32 (m, 2H, Ph); 8.73 (s, 1H, NH); 11.0 (d, 1H, NH).

The following are synthesized by the same method:

N-cyclopropylcarbonyl-N'-[2-cyclopropyl-1-(4-fluorophenyl)ethyl]thiourea Compound X.2

1H NMR (CDCl$_3$, δ ppm): 0.05–0.15 (m, 2H, c-Pr); 0.41–0.50 (m, 2H, c-Pr); 0.50–0.70 (m, 1H, c-Pr); 1.0–1.1 (m, 2H, c-Pr); 1.1–1.2 (m, 2H, c-Pr); 1.4–1.65 (m, 1H, c-Pr); 1.75–1.85 (m, 2H, CH$_2$-c-Pr); 5.40–5.50 (m, 1H, CH); 6.95–7.07 (m, 2H, Ph); 7.23–7.31 (m, 2H, Ph); 8.89 (s, 1H, NH); 11.05 (d, 1H, NH)

N-acetyl-N'-(2-methoxy-5-methylphenyl)thiourea Compound X.3

M.p.=152° C.

The compounds in the following TABLE 2 are also synthesized by the same method or by replacing benzene with chloroform:

TABLE 2

N-acylthioureas of formula X

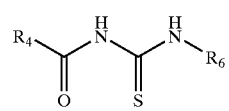

(X)

| Compound No. | R$_4$ | R$_6$ | $^1$H NMR (CDCl$_3$, δ ppm) |
|---|---|---|---|
| X.4 | cyclopropyl | 1-phenyl-2-cyclopropyl-ethyl | 0.04–0.14(m, 2H, c-Pr); 0.39–0.45(m, 2H, c-Pr): 0.48–0.68(m, 1H, c-Pr); 0.90–1.08(m, 2H, c-Pr); 1.08–1.15(m, 2H, c-Pr); 1.40–1.55(m, 1H, c-Pr); 1.75–1.85(m, 2H, CH$_2$—c-Pr); 5.41–5.52(m, 1H, CH); 7.15–7.40(m, 5H, Ph); 8.98(s, 1H, NH): 11.08(d, 1H, NH). |
| X.5 | cyclopropyl | 1-(4-methyl-3-fluorophenyl)-2-cyclopropyl-ethyl | 0.04–0.15(m, 2H, c-Pr); 0.39–0.50(m, 2H, c-Pr); 0.50–0.68(m, 1H, c-Pr); 0.90–1.02(m, 2H, c-Pr); 1.03–1.18(m, 2H, c-Pr); 1.40–1.52(m, 1H, c-Pr); 1.71–1.81(m, 2H, CH$_2$—c-Pr); 2.22(d, J=1.8 Hz, 3H, CH$_3$); 5.34–5.49(m, 1H, CH); 6.90–7.00(m, 2H, Ph); 7.08–7.20(m, 1H, Ph); 9.00(s, 1H, NH); 11.03(d, 1H, NH). |
| X.6 | cyclopropyl | 1-(3-fluoro-4-methylphenyl)-2-cyclopropyl-ethyl | 0.04–0.15(m, 2H, c-Pr); 0.39–0.50(m, 2H, c-Pr); 0.50–0.70(m, 1H, c-Pr); 0.90–1.03(m, 2H, c-Pr); 1.03–1.18(m, 2H, c-Pr); 1.40–1.52(m, 1H, c-Pr); 1.70–1.81(m, 2H, CH$_2$—c-Pr); 2.22(d, J=1.8 Hz, 3H, CH$_3$); 5.35–5.47(m, 1H, CH); 6.90–7.00(m, 2H, Ph); 7.08–7.20(m, 1H, Ph); 8,97(s, 1H, NH); 11.03(d, 1H, NH). |

TABLE 2-continued

N-acylthioureas of formula X (X)

| Compound No. | R₄ | R₆ | ¹H NMR (CDCl₃, δ ppm) |
|---|---|---|---|
| X.7 | cyclopropyl | 1-(4-fluorophenyl)-2-methoxyethyl (CH(CH₃) with CH₂OCH₃ and 4-F-Ph) | 0.88–1.02(m, 2H, c-Pr); 1.08–1.18(m, 2H, c-Pr); 1.40–1.52(m, 1H, c-Pr); 3.35(s, 3H, OCH₃); 3.62–3.75(m, 2H, CH₂O); 5.50–5.60(m, 1H, CH); 6.94–7.06(m, 2H, Ph); 7.26–7.35(m, 2H, Ph); 8.99(s, 1H, NH); 11.16(d, 1H, NH). |
| X.8 | —CH₂CH₃ | 1-phenylbutyl | 0.88–0.95(m, 3H, CH₃); 1.11–1.20(m, 3H, CH₃); 1.20–1.41(m, 2H, CH₂); 1.72–2.00(m, 2H, CH₂); 2.30–2.38(m, 2H, CH₂); 5.34–5.46(m, 1H, CH); 7.19–7.37(m, 5H, Ph); 8.73(s, 1H, NH); 10.95(d, 1H, NH). |
| X.9 | —CH₃ | 1-phenylbutyl | 0.88–0.95(m, 3H, CH₃); 1.22–1.40(m, 2H, CH₂); 1.71–2.02(m, 2H, CH₂); 2.10(s, 3H, CH₃); 5.33–5.45(m, 1H, CH); 7.19–7.37(m, 5H, Ph); 8.89(s, 1H, NH); 10.92(d, 1H, NH). |
| X.10 | —CH₃ | 1-(3-fluoro-4-methylphenyl)-2-cyclopropylethyl | 0.07–0.15(m, 2H, c-Pr); 0.39–0.49(m, 2H, c-Pr); 0.50–0.68(m, 1H, c-Pr); 1.74–1.85(m, 2H, CH₂—c-Pr); 2.10(s, 3H, CH₃); 2.22(d, J=1.8 Hz, 3H, CH₃); 5.36–5.46(m, 1H, CH); 6.90–7.00(m, 2H, Ph); 7.08–7.16(m, 1H, Ph); 8.69(s, 1H, NH); 10.96(d, 1H, NH). |
| X.11 | —CH₃ | 1-(4-fluorophenyl)-2-cyclopropylethyl | 0.02–0.17(m, 2H, c-Pr); 0.40–0.47(m, 2H, c-Pr); 0.48–0.65(m, 1H, c-Pr); 1.74–1.82(m, 2H, CH₂—c-Pr); 2.10(s, 3H, CH₃); 5.38–5.49(m, 1H, CH); 6.94–7.06(m, 2H, Ph); 7.21–7.31(m, 2H, Ph); 8.72(s, 1H, NH); 10.98(d, 1H, NH). |

TABLE 2-continued

N-acylthioureas of formula X

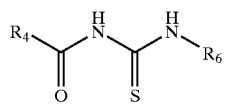

(X)

| Compound No. | R₄ | R₆ | ¹H NMR (CDCl₃, δ ppm) |
|---|---|---|---|
| X.12 | —CH₂CH₃ | (1-methyl-2-cyclopropylethyl group attached to 3-fluoro-4-methylphenyl) | 0.07–0.17(m, 2H, c-Pr); 0.39–0.49(m, 2H, c-Pr); 0.50–0.68(m, 1H, c-Pr); 1.12–1.23(m, 3H, CH₃); 1.74–1.82(m, 2H, CH₂—c-Pr); 2.22(d, J=1.8 Hz, 3H, CH₃); 2.27–2.39(m, 2H, CH₂); 5.36–5.46(m, 1H, CH); 6.91–7.00(m, 2H, Ph); 7.08–7.17(m, 1H, Ph); 8.52(s, 1H, NH); 10.97(d, 1H, NH). |
| X.13 | —CH₂CH₃ | (1-methyl-2-cyclopropylethyl group attached to 4-fluorophenyl) | 0.03–0.17(m, 2H, c-Pr); 0.41–0.49(m, 2H, c-Pr); 0.50–0.68(m, 1H, c-Pr); 1.12–1.22(m, 3H, CH₃); 1.74–1.82(m, 2H, CH₂—c-Pr); 2.27–2.39(m, 2H, CH₂); 5.39–5.49(m, 1H, CH); 6.95–7.06(m, 2H, Ph); 7.22–7.32(m, 2H, Ph); 8.77(s, 1H, NH); 10.98(d, 1H, NH). |
| X.14 | —c-Pr | (1-methylbutyl group attached to phenyl) | 0.87–1.02(m, 2H. c-Pr and 3H, CH₃); 1.02–1.15(m, 2H, c-Pr); 1.18–1.52(m, 1H, c-Pr and 2H, CH₂); 1.71–2.02(m, 2H, CH₂); 5.33–5.44(m, 1H, CH); 7.19–7.37(m, 5H, Ph); 9.05(s, 1H, NH); 10.97(d, 1H, NH) |
| X.15 | —CH₃ | (1-methyl-2-cyclopropylethyl group attached to 4-methylphenyl) | 0.04–0.17(m, 2H, c-Pr); 0.35–0.47(m, 2H, c-Pr); 0.48–0.65(m, 1H, c-Pr); 1.75–1.82(m, 2H, CH₂—c-Pr); 2.09(s, 3H, CH₃); 2.31(s, 3H, CH₃); 5.38–5.49(m, 1H, CH); 7.10–7.23(m, 4H, Ph); 8.69(s, 1H, NH); 10.95(d, 1H, NH). |
| X.16 | —CH₃ | (1-methyl-2-cyclopropylethyl group attached to 1,3-benzodioxol-5-yl) | 0.06–0.17(m, 2H, c-Pr); 0.40–0.50(m, 2H, c-Pr); 0.52–0.64(m, 1H, c-Pr); 1.75–1.82(m, 2H, CH₂—c-Pr); 2.14(s, 3H, CH₃); 5.38–5.45(m, 1H, CH); 5.97(s, 2H, OCH₂O); 6.77–6.83(m, 3H, Ph); 8.61(s, 1H, NH); 10.93(d, 1H, NH). |
| X.17 | —CH₃ | (1-methyl-2-cyclopropylethyl group attached to 4-(methoxymethyl)phenyl) | 0.07–0.20(m, 2H, c-Pr); 0.43–0.50(m, 2H, c-Pr); 0.58–0.68(m, 1H, c-Pr); 1.80–1.90(m, 2H, CH₂—c-Pr); 2.14(s, 3H, CH₃); 3.40(s, 3H, OCH₃); 4.45(s, 2H, CH₂—O); 5.47–5.55(m, 1H, CH); 7.28–7.35(m, 4H, Ph): 8.71(s, 1H, NH); 11.03(d, 1H, NH). |

TABLE 2-continued

N-acylthioureas of formula X $$R_4-\underset{O}{C}(-)-\underset{H}{N}-\underset{S}{C}(-)-\underset{H}{N}-R_6 \quad (X)$$

| Compound No. | R₄ | R₆ | ¹H NMR (CDCl₃, δ ppm) |
|---|---|---|---|
| X.18 | —CH₃ | 1-phenyl-2-cyclopropylethyl (CH with H, CH₂-cPr, Ph) | 0.07–0.20(m, 2H, c-Pr); 0.43–0.50(m, 2H, c-Pr); 0.58–0.70(m, 1H, c-Pr); 1.80–1.90(m, 2H, CH₂—c-Pr); 2.14(s, 3H, CH₃); 5.48–5.56(m, 1H, CH); 7.26–7.40(m, 5H, Ph); 8.67(s, 1H, NH); 11.04(d, 1H, NH). |
| X.19 | cyclopropyl | 1-(4-methylphenyl)pentyl (CH with H, propyl chain, p-tolyl) | 0.90–1.03(m, 2H. c-Pr and 3H, CH₃); 1.03–1.18(m, 2H, c-Pr); 1.25–1.50(m, 1H, cPr and 2H, CH₂); 1.75–2.0(m, 2H, CH₂); 2.34(s, 3H, CH₃); 5.34–5.43(m, 1H, CH); 7.14–7.22(m, 4H, Ph); 8.79(s, 1H, NH); 10.92(d, 1H, NH). |

2) Preparation of the N-acyl-S-methylisothioureas of Formula IX

First Method

N-acetyl-N'-[2-cyclopropyl-1-(4-fluorophenyl)ethyl]-S-methylisothiourea Compound IX.1

A solution of 2.8 g (10 mmol) of compound X.1 in 50 ml of tetrahydrofuran is stirred at 0° C. and 440 mg (11 mmol) of 60% sodium hydride in oil are added portionwise. After stirring for 20 minutes at 0° C., 0.75 ml (12 mmol) of methyl iodide are added. The reaction mixture is stirred for four hours at ambient temperature and is then cooled to 0° C., and 5 ml of ethanol and then 5 ml of water are slowly added. It is extracted with 150 ml of ethyl acetate and the organic phase is washed with water and then with water saturated with sodium chloride and dried over sodium sulphate, and the solvents are evaporated under reduced pressure. The crude residue (3.5 g) is used as is in the following stage (quantitative yield).

¹H NMR (CDCl₃, δ ppm): 0.05–0.15 (m, 2H, c-Pr); 0.43–0.55 (m, 2H, c-Pr); 0.55–0.75 (m, 1H, c-Pr); 1.70–1.85 (m, 2H, CH₂-c-Pr); 2.15 (s, 3H, CH₃CO); 2.42 (s, 3H, SCH₃); 4.62–4.71 (m, 1H, CH); 6.92–7.06 (m, 2H, Ph); 7.19–7.33 (m, 2H, Ph); 11.57 (s, 1H, NH).

The products in TABLE 3 are obtained by the same method.

TABLE 3

N-acyl-S-methylisothioureas of formula IX $$R_4-\underset{O}{C}(-)-N=\underset{S-CH_3}{C}-\underset{H}{N}-R_6 \quad (IX)$$

| Compound No. | R₄ | R₆ | ¹H NMR (CDCl₃, δ ppm) |
|---|---|---|---|
| IX.2 | cyclopropyl | 1-(4-fluorophenyl)-2-cyclopropylethyl | 0.05–0.11(m, 2H, c-Pr); 0.43–0.55(m, 2H, c-Pr); 0.55–0.72(m, 1H, c-Pr); 0.78–0.92(m, 2H, c-Pr); 1.05–1.10(m, 2H, c-Pr); 1.55–1.65(m, 1H, c-Pr); 1.70–1.80(m, 2H, CH₂—c-Pr); 2.42(s, 3H, SCH₃); 4.63–4.73(m, 1H, CH); 6.95–7.05(m, 2H, Ph); 7.18–7.31(m, 2H, Ph); 11.49(1H, NH) |

TABLE 3-continued

N-acyl-S-methylisothioureas of formula IX

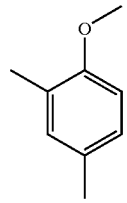

(IX)

| Compound No. | R₄ | R₆ | ¹H NMR (CDCl₃, δ ppm) |
|---|---|---|---|
| IX.3 | —CH₃ |  | 2.24 and 2.27(2s, 6H, CH₃ and CH₃CO); 2.40(s, 3H, SCH₃); 3.79(s, 3H, OCH₃); 6.80(d, J=8.3 Hz, 1H, Ph); 7.02(d, J=8.3 Hz, 1H, Ph); 7.18(s, 1H, Ph); 12.1(s, 1H, NH) |
| IX.4 | 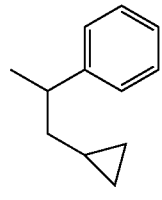 |  | 0.02–0.18(m, 2H, c-Pr); 0.38–0.50(m, 2H, c-Pr); 0.50–0.70(m, 1H, c-Pr); 0.75–0.95(m, 2H, c-Pr); 1.00–1.13(m, 2H, c-Pr); 1.50–1.65(m, 1H, c-Pr); 1.70–1.82(m, 2H, CH₂—c-Pr); 2.38(s, 3H, SCH₃); 4.62–4.75(m, 1H, CH); 7.15–7.40(m, 5H, Ph); 11.53(s, 1H, NH). |
| IX.5 | 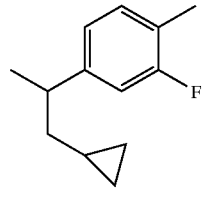 |  | 0.04–0.12(m, 2H, c-Pr); 0.40–0.50(m, 2H, c-Pr); 0.50–0.70(m, 1H, c-Pr); 0.78–0.90(m, 2H, c-Pr); 1.02–1.10(m, 2H, c-Pr); 1.52–1.82(m, 1H, c-Pr and 2H, CH₂—c-Pr); 2.23(d, J=1.8 Hz, 3H, CH₃); 2.38(s, 3H, SCH₃) 4.60–4.70(m, 1H, CH); 6.86–6.97(m, 2H, Ph); 7.08–7.20(m, 1H, Ph); 11.46(s, 1H, NH). |
| IX.6 | 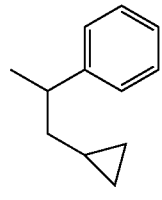 | 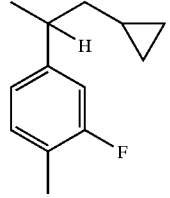 | 0.04–0.12(m, 2H, c-Pr); 0.40–0.50(m, 2H, c-Pr); 0.50–0.70(m, 1H, c-Pr); 0.78–0.90(m, 2H, c-Pr); 1.00–1.09(m, 2H, c-Pr); 1.52–1.82(m, 1H, c-Pr and 2H, CH₂—c-Pr); 2.23(d, J=1.8 Hz, 3H, CH₃); 2.38(s, 3H, SCH₃); 4.60–4.70(m, 1H, CH); 6.86–6.97(m, 2H, Ph); 7.08–7.20(m, 1H, Ph); 11.47(s, 1H, NH). |
| IX.7 |  | 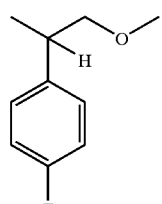 | 0.78–0.90(m, 2H, c-Pr); 1.03–1.11(m, 2H, c-Pr); 1.58–1.72(m, 1H, c-Pr); 2.37(s, 3H, SCH₃); 3.35(s, 3H, OCH₃); 3.52–3.65(m, 2H, CH₂O); 4.74–4.85(m, 1H, CH); 6.95–7.10(m, 2H, Ph); 7.15–7.30(m, 2H, Ph); 11.50(s, 1H, NH). |

Second Method

S-methyl-N-[(1S)-1-phenylbutyl]-N'-propionylisothiourea Compound IX.8

A solution of 6.4 g (24.2 mmol) of compound X.8 in 120 ml of dimethylformamide is stirred at ambient temperature and 7.9 g (24.2 mmol) of caesium carbonate are added. Subsequently, 3 ml (24 mmol) of iodomethane are slowly added. The mixture is stirred at ambient temperature for two hours, ice is then added and extraction is carried out with ethyl acetate. The organic phase is washed with water and then with water saturated with sodium chloride and dried over sodium sulphate, and the solvents are evaporated under reduced pressure. The crude residue is purified by chromatography on a column of silica gel (eluent: 9/1 (v/v) cyclohexane/ethyl acetate). 5.15 g of compound IX.8 are obtained. Yield 72%.

¹H NMR (CDCl₃, δ ppm): 0.86–0.94 (m, 3H, CH₃); 1.09–1.17 (m, 3H, CH₃); 1.22–1.45 (m, 2H, CH₂); 1.72–1.86 (m, 2H, CH₂); 2.38 (s, 3H, SCH₃); 2.35–2.50 (m, 2H, CH₂); 4.57–4.63 (m, 1H, CH); 7.19–7.37 (m, 5H, Ph); 11.52 (s, 1H, NH).

The products in TABLE 4 are obtained by the same method.

TABLE 4

N-acyl-S-methylisothioureas of formula IX (IX)

| Compound No. | $R_4$ | $R_6$ | $^1$H NMR (CDCl$_3$, δ ppm) |
|---|---|---|---|
| IX.9 | —CH$_3$ | 1-phenylbutyl | 0.85–0.95(m, 3H, CH$_3$); 1.20–1.48(m, 2H, CH$_2$); 1.65–1.88(m, 2H, CH$_2$); 2.15(s, 3H, CH$_3$); 2.38(s, 3H, SCH$_3$); 4.55–4.65(m, 1H, CH); 7.18–7.37(m, 5H, Ph); 11.53(s, 1H, NH). |
| IX.10 | —CH$_3$ | 1-(3-fluoro-4-methylphenyl)-2-cyclopropylethyl | 0.07–0.15(m, 2H, c-Pr); 0.42–0.51(m, 2H, c-Pr); 0.52–0.68(m, 1H, c-Pr); 1.70–1.90(m, 2H, CH$_2$—c-Pr); 2.16(s, 3H, CH$_3$); 2.23(d, J=1.8 Hz, 3H, CH$_3$); 2.39(s, 3H, SCH$_3$); 4.62–4.70(m, 1H, CH); 6.86–6.95(m, 2H, Ph); 7.08–7.16(m, 1H, Ph); 11.56(s, 1H, NH). |
| IX.11 | —CH$_3$ | 1-(4-fluorophenyl)-2-cyclopropylethyl | 0.08–0.20(m, 2H, c-Pr); 0.42–0.55(m, 2H, c-Pr); 0.56–0.72(m, 1H, c-Pr); 1.68–1.88(m, 2H, CH$_2$—c-Pr); 2.20(s, 3H, CH$_3$); 2.48(s, 3H, SCH$_3$); 4.74–4.80(m, 1H, CH); 7.03–7.12(m, 2H, Ph); 7.25–7.31(m, 2H, Ph): 11.67(s, 1H, NH). |
| IX.12 | —CH$_2$CH$_3$ | 1-(3-fluoro-4-methylphenyl)-2-cyclopropylethyl | 0.05–0.15(m, 2H, c-Pr); 0.40–0.50(m, 2H, c-Pr); 0.52–0.70(m, 1H, c-Pr); 1.10–1.20(m, 3H, CH$_3$); 1.60–1.80(m, 2H, CH$_2$—c-Pr); 2.22(d, J=1.8 Hz, 3H, CH$_3$); 2.38(s, 3H, SCH$_3$); 2.35–2.50(m, 2H, CH$_2$); 4.60–4.70(m, 1H, CH); 6.87–6.95(m, 2H, Ph); 7.08–7.17(m, 1H, Ph); 11.52(s, 1H, NH). |
| IX.13 | —CH$_2$CH$_3$ | 1-(4-fluorophenyl)-2-cyclopropylethyl | 0.05–0.15(m, 2H, c-Pr); 0.40–0.50(m, 2H, c-Pr); 0.50–0.70(m, 1H, c-Pr); 1.10–1.20(m, 3H, CH$_3$); 1.60–1.82(m, 2H, CH$_2$—c-Pr); 2.38(s, 3H, SCH$_3$); 2.35–2.53(m, 2H, CH$_2$); 4.65–4.72(m, 1H, CH); 6.94–7.06(m, 2H, Ph); 7.17–7.27(m, 2H, Ph); 11.50(s, 1H, NH). |
| IX.14 | cyclopropyl | 1-phenylbutyl | 0.78–0.98(m, 2H, c-Pr and 3H, CH$_3$); 1.00–1.08(m, 2H, c-Pr); 1.25–1.45(m, 2H, CH$_2$); 1.65–1.88(m, 1H, c-Pr and 2H, CH$_2$); 2.37(s, 3H, SCH$_3$); 4.55–4.65(m, 1H, CH); 7.18–7.36(m, 5H, Ph); 11.45(s, 1H, NH). |

TABLE 4-continued

N-acyl-S-methylisothioureas of formula IX (IX)

R4—C(=O)—N=C(SMe)—NH—R6

| Compound No. | R4 | R6 | ¹H NMR (CDCl₃, δ ppm) |
|---|---|---|---|
| IX.15 | —CH₃ | 1-(4-methylphenyl)-2-cyclopropylethyl | 0.05–0.15(m, 2H, c-Pr); 0.40–0.52(m, 2H, c-Pr); 0.53–0.70(m, 1H, c-Pr); 1.60–1.82(m, 2H, CH₂—c-Pr); 2.15(s, 3H, CH₃); 2.31(s, 3H, CH₃); 2.37(s, 3H, SCH₃); 4.60–4.70(m, 1H, CH); 7.08–7.23(m, 4H, Ph); 11.59(s, 1H, NH). |
| IX.16 | —CH₃ | 1-(3,4-methylenedioxyphenyl)-2-cyclopropylethyl | 0.06–0.17(m, 2H, c-Pr); 0.42–0.55(m, 2H, c-Pr); 0.56–0.70(m, 1H, c-Pr); 1.65–1.80(m, 2H, CH₂—c-Pr); 2.19(s, 3H, CH₃); 2.43(s, 3H, SCH₃); 4.60–4.70(m, 1H, CH); 5.97(s, 2H, OCH₂O); 6.73–6.81(m, 3H, Ph); 11.58(s, 1H, NH). |
| IX.17 | —CH₃ | 1-(4-methoxymethylphenyl)-2-cyclopropylethyl | 0.10–0.18(m, 2H, c-Pr); 0.45–0.52(m, 2H, c-Pr); 0.60–0.70(m, 1H, c-Pr); 1.70–1.85(m, 2H, CH₂—c-Pr); 2.20(s, 3H, CH₃); 2.42(s, 3H, SCH₃); 3.40(s, 3H, OCH₃); 4.45(s, 2H, CH₂—O); 4.70–4.80(m, 1H, CH); 7.25–7.35(m, 4H, Ph); 11.65(s, 1H, NH). |
| IX.18 | —CH₃ | 1-phenyl-2-cyclopropylethyl | 0.08–0.20(m, 2H, c-Pr); 0.43–0.55(m, 2H, c-Pr); 0.60–0.72(m, 1H, c-Pr); 1.63–1.88(m, 2H, CH₂—c-Pr); 2.20(s, 3H, CH₃); 2.43(s, 3H, SCH₃); 4.66–4.77(m, 1H, CH); 7.28–7.40(m, 5H, Ph); 11.66(s, 1H, NH). |
| IX.19 | cyclopropyl | 1-(4-methylphenyl)butyl | 0.80–0.87(m, 2H, c-Pr); 0.87–0.97(m, 3H, CH₃); 1.02–1.10(m, 2H, c-Pr); 1.25–1.48(m, 1H, c-Pr and 2H, CH₂); 1.70–1.85(m, 2H, CH₂); 2.33(s, 3H, CH₃); 2.40(s, 3H, SCH₃); 4.52–4.62(m, 1H, CH); 7.10–7.20(m, 4H, Ph); 11.45(s, 1H, NH). |

3) Preparation of the NH Aminotriazoles of Formula VIII 1-(2-Chloro-4-methoxy-5-methylphenyl)-N-[2-cyclopropyl-1-(4-fluorophenyl)ethyl]-5-methyl-1H-1,2,4-triazol-3-amine Compound VIIX.1

3 g (11.5 mmol) of 2-chloro-4-methoxy-5-methylphenylhydrazine hydrochloride (compound III.1) are added to a solution of 3.2 g (10 mmol) of compound IX.1 in 25 ml of toluene, followed by 3.5 ml (25 mmol) of triethylamine and by 4 Å molecular sieve. The reaction mixture is stirred overnight at moderate reflux and is then cooled. The molecular sieve is removed by filtration and the filtrate is diluted with 100 ml of ethyl acetate. The organic phase is washed with 1N hydrochloric acid, with water, with a saturated aqueous sodium hydrogencarbonate solution, with water and then with water saturated with sodium chloride. It is dried over sodium sulphate and then the solvents are evaporated under reduced pressure. The crude residue is purified by chromatography on a column of silica gel (eluent: 3/1 then 2/1 then 1/1 (v/v) cyclohexane/ethyl acetate). 1.35 g of compound VIII.1 are obtained. Yield 32%.

¹H NMR (CDCl₃, δ ppm): 0.02–0.12 (m, 2H, c-Pr); 0.35–0.45 (m, 2H, c-Pr); 0.55–0.70 (m, 1H, c-Pr); 1.60–1.82 (m, 2H, CH₂-c-Pr); 2.17 (s, 6H, 2CH₃); 3.83 (s, 3H, OCH₃); 4.60 (d, J=8.2 Hz, 1H, NH); 4.73–4.84 (m, 1H, CH); 6.85 (s, 1H, Ph); 6.90–7.00 (m, 2H, Ph); 7.05 (s, 1H, Ph); 7.25–7.37 (m, 2H, Ph).

The compounds VIII in TABLE 5 were prepared by the same method. The toluene can be replaced by xylene, dimethylformamide or dimethyl sulphoxide. When a base is needed, triethylamine can be replaced by N,N-diethylaniline or caesium carbonate.

TABLE 5

NH aminotriazoles of formula VIII (VIII)

| Compound No. | R₁, R₂, R₃ | R₄ | R₆ | ¹H NMR (CDCl₃, δ ppm) |
|---|---|---|---|---|
| VIII.2 | 2-Cl 4-OCH₃ 5-CH₃ | c-Pr | 1-(4-F-phenyl)-2-cyclopropylethyl | 0.0–0.10(m, 2H, c-Pr); 0.35–0.45(m, 2H, c-Pr); 0.52–0.70(m, 1H, c-Pr); 0.83–0.97(m, 2H, c-Pr); 1.0–1.05(m, 2H, c-Pr); 1.40–1.52(m, 1H, c-Pr); 1.60–1.85(m, 2H, CH₂-c-Pr); 2.15(s, 3H, CH₃); 3.83(s, 3H, OCH₃); 4.49(d, J=8.2 Hz, 1H, NH); 4.68–4.82(m, 1H, CH); 6.87(s, 1H, Ph); 6.90–6.99(m, 2H, Ph); 7.11(s, 1H, Ph); 7.20–7.34(m, 2H, Ph). |
| VIII.3 | 2-Cl 4-Cl H | —CH₃ | 2,4-dimethyl-methoxyphenyl | 2.28(s, 6H, 2CH₃); 3.83(s, 3H, OCH₃); 6.62(dd, J₁=8.1 Hz, J₂=1.5 Hz, 1H, Ph); 6.73(d, J=8.1 Hz, 1H, Ph); 7.18(s, 1H, NH); 7.37–7.41(m, 2H, Ph); 7.57(d, J=18 Hz, 1H, Ph); 7.89(d, J=1.9 Hz, 1H, Ph). |
| VIII.4 | 2-Cl 4-CF₃ 6-Cl | c-Pr | 1-(4-F-phenyl)-2-cyclopropylethyl | 0.02–0.10(m, 2H, c-Pr); 0.35–0.45(m, 2H, c-Pr); 0.52–0.70(m, 1H, c-Pr); 0.83–1.04(m, 2H, c-Pr); 1.05–1.20(m, 2H, c-Pr); 1.25–1.42(m, 1H, c-Pr); 1.60–1.85(m, 2H, CH₂—c-Pr); 4.65–4.82(m, 2H, CH and NH); 6.90–7.01(m, 2H, Ph); 7.25–7.45(m, 2H, Ph); 7.63–7.70(m, 2H, Ph) |
| VIII.5 | 2-Cl 4-Cl H | c-Pr | 1-phenyl-2-cyclopropylethyl | 0.02–0.12(m, 2H, c-Pr); 0.35–0.47(m, 2H c-Pr); 0.52–0.70(m, 1H, c-Pr); 0.80–0.98(m, 2H, c-Pr); 1.0–1.10(m, 2H, c-Pr); 1.38–1.50(m, 1H, c-Pr); 1.60–1.85(m, 2H, CH₂—c-Pr); 4.58(d, J=8.2 Hz, 1H, NH); 4.69–4.81(m, 1H, CH); 7.10–7.40(m, 7H, Ph); 7.50(s, 1H, Ph). |
| VIII.6 | 2-Cl 4-OCH₃ 5-CH₃ | c-Pr | 1-phenyl-2-cyclopropylethyl | 0.0–0.10(m, 2H, c-Pr); 0.32–0.42(m, 2H, c-Pr); 0.52–0.70(m, 1H, c-Pr); 0.83–0.97(m, 2H, c-Pr); 1.0–1.10(m, 2H, c-Pr); 1.40–1.54(m, 1H, c-Pr); 1.60–1.87(m, 2H, CH₂—c-Pr); 2.16(s, 3H, CH₃); 3.83(s, 3H, OCH₃); 4.55(d, J=8.5 Hz, 1H, NH); 4.73–4.84(m, 1H, CH); 6.87(s, 1H, Ph); 7.13–7.38(m, 6H, Ph). |

TABLE 5-continued

NH aminotriazoles of formula VIII

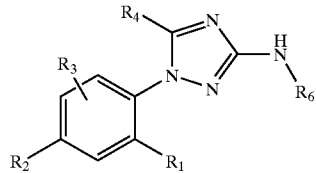
(VIII)

| Compound No. | $R_1, R_2, R_3$ | $R_4$ | $R_6$ | $^1$H NMR (CDCl$_3$, δ ppm) |
|---|---|---|---|---|
| VIII.7 | 2-Cl<br>4-OCH$_3$<br>5-CH$_3$ | c-Pr | 1-(4-methyl-3-fluorophenyl)-2-cyclopropyl-ethyl | 0.02–0.10(m, 2H, c-Pr); 0.35–0.45(m, 2H, c-Pr); 0.52–0.70(m, 1H, c-Pr); 0.85–0.97(m, 2H, c-Pr); 0.99–1.07(m, 2H, c-Pr); 1.40–1.52(m, 1H, c-Pr); 1.60–1.85(m, 2H, CH$_2$—c-Pr); 2.16(s, 3H, CH$_3$); 2.21(d, J=1.8 Hz, 3H, CH$_3$); 3.83(s, 3H, OCH$_3$); 4.48(d, J=8.2 Hz, 1H, NH); 4.68–4.80(m, 1H, CH); 6.87(s, 1H, Ph); 6.96–7.15(m, 4H, Ph). |
| VIII.8 | 2-Cl<br>4-OCH$_3$<br>5-CH$_3$ | c-Pr | 1-(3-fluoro-4-methylphenyl)-2-cyclopropyl-ethyl | 0.02–0.10(m, 2H, c-Pr); 0.35–0.45(m, 2H, c-Pr); 0.53–0.70(m, 1H, c-Pr); 0.85–0.97(m, 2H, c-Pr); 1.0–1.08(m, 2H, c-Pr); 1.40–1.52(m, 1H, c-Pr); 1.60–1.85(m, 2H, CH$_2$—c-Pr); 2.16(s, 3H, CH$_3$); 2.21(d, J=1.8 Hz, 3H, CH$_3$); 3.83(s, 3H, OCH$_3$); 4.49(d, J=8.2 Hz, 1H, NH); 4.68–4.80(m, 1H, CH); 6.87(s, 1H, Ph); 6.97–7.15(m, 4H, Ph). |
| VIII.9 | 2-Cl<br>4-OCH$_3$<br>5-CH$_3$ | c-Pr | 1-(4-fluorophenyl)-2-methoxyethyl | 0.83–0.97(m, 2H, c-Pr), 1.0–1.10(m, 2H, c-Pr); 1.40–1.52(m, 1H, c-Pr); 2.15(s, 3H, CH$_3$); 3.32(s, 3H, OCH$_3$); 3.58–3.72(m, 2H, CH$_2$O); 3.83(s, 3H, OCH$_3$); 4.78–4.86(m, 2H, CH and NH); 6.85(s, 1H, Ph); 6.87–7.00(m, 2H, Ph); 7.12(s, 1H, Ph); 7.27–7.40(m, 2H, Ph). |
| VIII.10 | 2-Cl<br>4-Cl<br>H | c-Pr | 1-(4-methyl-3-fluorophenyl)-2-cyclopropyl-ethyl | (d$_6$-DMSO, δ ppm): −0.04–0.10(m, 2H, c-Pr); 0.25–0.40(m, 2H, c-Pr); 0.55–0.70(m, 1H, c-Pr); 0.80–0.95(m, 4H, c-Pr); 1.35–1.78(m, 3H, c-Pr and CH$_2$—c-Pr); 2.14(d, J=1.5 Hz, 3H, CH$_3$); 4.39–4.51(m, 1H, CH); 6.57(d, J=9.1 Hz, 1H, NH); 7.00–7.15(m, 3H, Ph); 7.55(s, 2H, Ph); 7.85(s, 1H, Ph). |
| VIII.11 | 2-Cl<br>4-Cl<br>H | c-Pr | 1-(4-fluorophenyl)-2-methoxyethyl | 0.85–1.02(m, 2H, c-Pr); 1.02–1.12(m, 2H, c-Pr); 1.40–1.52(m, 1H, c-Pr); 3.32(s, 3H, OCH$_3$); 3.53–3.70(m, 2H, CH$_2$O); 4.73–4.82(m, 1H, CH); 4.91(d, J=6.7 Hz, 1H, NH); 6.90–7.00(m, 2H, Ph); 7.26–7.40(m, 4H, Ph); 7.50(s, 1H, Ph). |
| VIII.12 | 2-CH$_3$<br>4-CH$_3$<br>H | c-Pr | 1-(3-fluoro-4-methylphenyl)-2-cyclopropyl-ethyl | 0.02–0.10(m, 2H, c-Pr); 0.35–0.45(m, 2H, c-Pr); 0.55–0.70(m, 1H, c-Pr); 0.83–0.97(m, 2H, c-Pr); 1.0–1.10(m, 2H, c-Pr); 1.42–1.55(m, 1H, c-Pr); 1.60–1.80(m, 2H, CH$_2$—c-Pr); 1.94(s, 3H, CH$_3$); 2.20(d, J=1.8 Hz, 3H, CH$_3$); 2.32(s, 3H, CH$_3$); 4.54(d, J=8.2 Hz, 1H, NH); 4.64–4.75(m, 1H, CH); 6.97–7.15(m, 6H, Ph). |

TABLE 5-continued

NH aminotriazoles of formula VIII

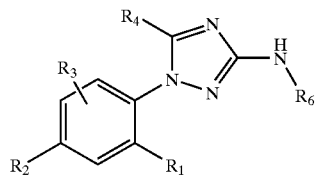

(VIII)

| Compound No. | $R_1, R_2, R_3$ | $R_4$ | $R_6$ | $^1$H NMR (CDCl$_3$, δ ppm) |
|---|---|---|---|---|
| VIII.13 | 2-Cl<br>4-Cl<br>H | —CH$_2$CH$_3$ | 1-phenylbutyl | 0.85–0.95(m, 3H, CH$_3$); 1.11–1.20(m, 3H, CH$_3$); 1.20–1.45(m, 2H, CH$_2$); 1.70–1.95(m, 2H, CH$_2$); 2.35–2.48(m, 2H, CH$_2$); 4.47(d, J=8.5 Hz, 1H, NH); 4.60–4.71(m, 1H, CH); 7.14–7.37(m, 7H, Ph); 7.50(s, 1H, Ph). |
| VIII.14 | 2-Cl<br>4-OCH$_3$<br>5-CH$_3$ | —CH$_3$ | 1-phenylbutyl | 0.86–0.96(m, 3H, CH$_3$); 1.22–1.45(m, 2H, CH$_2$); 1.70–1.90(m, 2H, CH$_2$); 2.16(s, 6H, CH$_3$); 3.84(s, 3H, OCH$_3$); 4.39(d, J=8.8 Hz, 1H, NH); 4.66–4.77(m, 1H, CH); 6.86(s, 1H, Ph); 7.09(s, 1H, Ph); 7.15–7.38(m, 5H, Ph). |
| VIII.15 | 2-Cl<br>4-OCH$_3$<br>5-CH$_3$ | —CH$_3$ | 1-(3-fluoro-4-methylphenyl)-2-cyclopropylethyl | 0.02–0.10(m, 2H, c-Pr); 0.36–0.46(m, 2H, c-Pr); 0.55–0.72(m, 1H, c-Pr); 1.60–1.85(m, 2H, CH$_2$—c-Pr); 2.15(s, 6H, CH$_3$); 2.21(d, J=1.8 Hz, 3H, CH$_3$); 3.83(s, 3H, OCH$_3$); 4.65–4.85(m, 2H, CH and NH); 6.87(s, 1H, Ph); 6.99–7.12(m, 4H, Ph). |
| VIII.16 | 2-Cl<br>4-Cl<br>H | —CH$_3$ | 1-(4-fluorophenyl)-2-cyclopropylethyl | 0.02–0.13(m, 2H, c-Pr); 0.35–0.46(m, 2H, c-Pr); 0.55–0.70(m, 1H, c-Pr): 1.61–1.85(m, 2H, CH$_2$—c-Pr); 2.17(s, 3H, CH$_3$); 4.68–4.80(m, 2H, CH and NH); 6.90–7.01(m, 2H, Ph); 7.21–7.36(m, 4H, Ph) 7.50(d, J=2 Hz, 1H, Ph). |
| VIII.17 | 2-Cl<br>4-OCH$_3$<br>5-CH$_3$ | —CH$_2$CH$_3$ | 1-(3-fluoro-4-methylphenyl)-2-cyclopropylethyl | 0.02–0.12(m, 2H, c-Pr); 0.36–0.46(m, 2H, c-Pr); 0.55–0.72(m, 1H, c-Pr); 1.19(t, J=7.6 Hz, 3H, CH$_3$); 1.64–1.89(m, 2H, CH$_2$—c-Pr); 2.15(s, 3H, CH$_3$); 2.21(d, J=1.8 Hz, 3H, CH$_3$); 2.45(q, J=7.6 Hz, 2H, CH$_2$); 3.83(s, 3H, OCH$_3$); 4.68–4.88(m, 2H, CH and NH); 6.86(s, 1H, Ph); 6.99–7.12(m, 4H, Ph). |
| VIII.18 | 2-Cl<br>4-Cl<br>H | —CH$_2$CH$_3$ | 1-(4-fluorophenyl)-2-cyclopropylethyl | 0.02–0.12(m, 2H, c-Pr); 0.36–0.52(m, 2H, c-Pr); 0.55–0.72(m, 1H, c-Pr); 1.14–1.24(m, 3H, CH$_3$); 1.60–1.85(m, 2H, CH$_2$—c-Pr); 2.36–2.48(m, 2H, CH$_2$); 4.68–4.80(m, 2H, CH and NH); 6.91–7.02(m, 2H, Ph); 7.20–7.36(m, 4H, Ph); 7.48(d, J=2 Hz, 1H, Ph). |

TABLE 5-continued

NH aminotriazoles of formula VIII

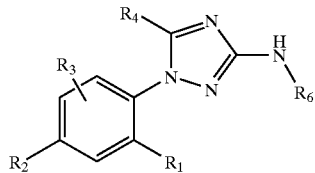

(VIII)

| Compound No. | $R_1, R_2, R_3$ | $R_4$ | $R_6$ | $^1$H NMR (CDCl$_3$, δ ppm) |
|---|---|---|---|---|
| VIII.19 | 2-Cl<br>4-Cl<br>H | —◁ (c-Pr) | CH(CH$_2$CH$_2$CH$_3$)-Ph | 0.83–0.97(m, 3H, CH$_3$ and 2H, c-Pr); 1.0–1.10(m, 2H, c-Pr); 1.30–1.52(m, 1H, c-Pr and 2H, CH$_2$); 1.65–1.90(m, 2H, CH$_2$); 4.41(d, J=8.4 Hz, 1H, NH); 4.55–4.68(m, 1H, CH); 7.14–7.37(m, 7H, Ph); 7.50(d, J=2 Hz, 1H, Ph). |
| VIII.20 | 2-Cl<br>4-OCH$_3$<br>5-CH$_3$ | —CH$_2$CH$_3$ | CH(CH$_2$-c-Pr)-C$_6$H$_4$-4-F | 0.00–0.12(m, 2H, c-Pr); 0.35–0.50(m, 2H, c-Pr); 0.52–0.70(m, 1H, c-Pr); 1.17(t, J=7.6 Hz, 3H, CH$_3$); 1.55–1.90(m, 2H, CH$_2$—c-Pr); 2.15(s, 3H, CH$_3$); 2.41(q, J=7.6 Hz, 2H, CH$_2$); 3.83(s, 3H, OCH$_3$); 4.60(d, J=8.4 Hz, 1H, NH); 4.66–4.83(m, 1H, CH); 6.86(s, 1H, Ph); 6.90–7.04(m, 2H, Ph); 7.10(s, 1H, Ph); 7.22–7.35(m, 2H, Ph). |
| VIII.21 | 2-Cl<br>4-Cl<br>H | —CH$_3$ | CH(CH$_2$-c-Pr)-C$_6$H$_4$(3-F, 4-CH$_3$) | 0.02–0.12(m, 2H, c-Pr); 0.36–0.46(m, 2H, c-Pr); 0.55–0.70(m, 1H, c-Pr); 1.60–1.85(m, 2H, CH$_2$—c-Pr); 2.15(s, 3H, CH$_3$); 2.21(d, J=1.8 Hz, 3H, CH$_3$); 4.62–4.80(m, 2H, CH and NH); 6.93–7.12(m, 3H, Ph); 7.23–7.36(m, 2H, Ph); 7.50(d, J=2 Hz, 1H, Ph). |
| VIII.22 | 2-Cl<br>4-OCH$_3$<br>5-CH$_3$ | —CH$_3$ | CH(CH$_2$-c-Pr)-C$_6$H$_4$-4-CH$_3$ | 0.02–0.10(m, 2H, c-Pr); 0.36–0.44(m, 2H, c-Pr); 0.55–0.70(m, 1H, c-Pr); 1.60–1.90(m, 2H, CH$_2$—c-Pr); 2.15(s, 6H, CH$_3$), 2.30(s, 3H, CH$_3$); 3.83(s, 3H, OCH$_3$); 4.65–4.85(m, 2H, CH and NH); 6.87(s, 1H, Ph); 7.07–7.12(m, 3H, Ph); 7.23–7.27(m, 2H, Ph). |
| VIII.23 | 2-Cl<br>4-Cl<br>H | —CH$_3$ | CH(CH$_2$-c-Pr)-C$_6$H$_4$-4-CH$_3$ | 0.02–0.10(m, 2H, c-Pr); 0.36–0.48(m, 2H, c-Pr); 0.55–0.72(m, 1H, c-Pr); 1.60–1.88(m, 2H, CH$_2$—c-Pr); 2.15(s, 3H, CH$_3$); 2.30(s, 3H, CH$_3$); 4.60(d, J=8.6 Hz, 1H, NH); 4.70–4.85(m, 1H, CH); 7.07–7.12(m, 2H, Ph); 7.23–7.30(m, 4H, Ph); 7.50(d, J=2 Hz, 1H, Ph). |
| VIII.24 | 2-Cl<br>4-OCH$_3$<br>5-CH$_3$ | —◁ (c-Pr) | CH(CH$_2$CH$_2$CH$_3$)-Ph | 0.85–0.97(m, 3H, CH$_3$ and 2H, c-Pr); 1.0–1.08(m, 2H, c-Pr); 1.25–1.53(m, 1H, c-Pr and 2H, CH$_2$); 1.62–1.90(m, 2H, CH$_2$); 2.15(s, 3H, CH$_3$); 3.83(s, 3H, OCH$_3$); 4.34(d, J=8.6 Hz, 1H, NH); 4.60–4.72(m, 1H, CH); 6.87(s, 1H, Ph); 7.13(s, 1H, Ph); 7.17–7.34(m, 5H, Ph). |

TABLE 5-continued

NH aminotriazoles of formula VIII

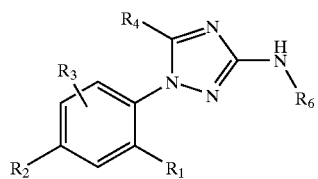

(VIII)

| Compound No. | $R_1, R_2, R_3$ | $R_4$ | $R_6$ | $^1$H NMR (CDCl$_3$, δ ppm) |
|---|---|---|---|---|
| VIII.25 | 2-Cl<br>4-OCH$_3$<br>5-CH$_3$ | —CH$_3$ | (1-methyl-2-cyclopropyl-ethyl)-(4-fluorophenyl) | 0.00–0.10(m, 2H, c-Pr); 0.35–0.46(m, 2H, c-Pr); 0.53–0.70(m, 1H, c-Pr); 1.55–1.80(m, 2H, CH$_2$—c-Pr); 2.14(s, 6H, CH$_3$); 3.83(s, 3H, OCH$_3$); 4.60(d, J=8.4 Hz, 1H, NH); 4.73–4.85(m, 1H, CH); 6.85(s, 1H, Ph); 6.90–7.05(m, 2H, Ph); 7.12(s, 1H, Ph); 7.24–7.35(m, 2H, Ph). |
| VIII.26 | 2-Cl<br>4-CF$_3$<br>H | —CH$_3$ | (1-methyl-2-cyclopropyl-ethyl)-(3-fluoro-4-methylphenyl) | 0.05–0.15(m, 2H, c-Pr); 0.42–0.48(m, 2H, c-Pr); 0.62–0.75(m, 1H, c-Pr); 1.65–1.85(m, 2H, CH$_2$—c-Pr); 2.26(d, J=1.8 Hz, 3H, CH$_3$); 2.30(s, 3H, CH$_3$); 4.72–4.79(m, 1H, CH); 5.0–5.15(m, 1H, NH); 7.00–7.17(m, 3H, Ph); 7.51(d, J=8.4 Hz; 1H, Ph); 7.66(d, J=8.4 Hz; 1H, Ph); 7.82(s, 1H, Ph). |
| VIII.27 | 2-Cl<br>4-OCH$_3$<br>5-CH$_3$ | —CH$_3$ | (1-methyl-2-cyclopropyl-ethyl)-(benzodioxole) | 0.05–0.15(m, 2H, c-Pr); 0.40–0.48(m, 2H, c-Pr); 0.60–0.72(m, 1H, c-Pr); 1.65–1.87(m, 2H, CH$_2$—c-Pr); 2.19(s, 6H, CH$_3$); 3.80(s, 3H, OCH$_3$); 4.62(d, J=8.4 Hz, 1H, NH); 4.72–4.80(m, 1H, CH); 5.94(s, 2H, OCH$_2$O); 6.75(d, J=8.1 Hz; 1H, Ph); 6.81–6.90(m, 3H, Ph); 7.12(s, 1H, Ph). |
| VIII.28 | 2-Cl<br>4-Cl<br>H | —CH$_3$ | (1-methyl-2-cyclopropyl-ethyl)-(benzodioxole) | 0.08–0.16(m, 2H, c-Pr); 0.42–0.50(m, 2H, c-Pr); 0.62–0.77(m, 1H, c-Pr); 1.62–1.87(m, 2H, CH$_2$—c-Pr); 2.23(s, 3H, CH$_3$); 4.62–4.80(m, 2H, CH and NH); 5.95(s, 2H, OCH$_2$O); 6.77(d, J=8 Hz; 1H, Ph); 6.86–6.91(m, 2H, Ph); 7.30–7.41(m, 2H, Ph); 7.56(d, J=1.9 Hz, 1H, Ph). |
| VII.29 | 2-Cl<br>4-OCH$_3$<br>5-CH$_3$ | —CH$_3$ | (1-methyl-2-cyclopropyl-ethyl)-(4-methoxymethylphenyl) | 0.07–0.15(m, 2H, c-Pr); 0.40–0.48(m, 2H, c-Pr); 0.60–0.75(m, 1H, c-Pr); 1.65–1.95(m, 2H, CH$_2$—c-Pr); 2.20(s, 3H, CH$_3$); 2.21(s, 3H, CH$_3$); 3.41(s, 3H, OCH$_3$); 3.89(s, 3H, OCH$_3$); 4.46(s, 2H, CH$_2$O); 4.82–4.92(m, 2H, CH and NH); 6.91(s, 1H, Ph); 7.12(s, 1H, Ph); 7.28–7.32(m, 2H, Ph) 7.38–7.42(m, 2H, Ph). |

TABLE 5-continued

NH aminotriazoles of formula VIII

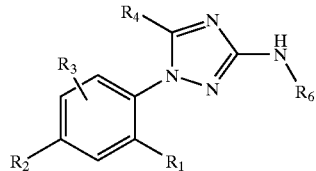

(VIII)

| Compound No. | $R_1, R_2, R_3$ | $R_4$ | $R_6$ | $^1$H NMR (CDCl$_3$, δ ppm) |
|---|---|---|---|---|
| VIII.30 | 2-Cl<br>4-OCH$_3$<br>H | —CH$_3$ | (1-methyl-2-cyclopropylethyl group attached to 3-fluoro-4-methylphenyl) | 0.07–0.14(m, 2H, c-Pr); 0.40–0.50(m, 2H, c-Pr); 0.62–0.77(m, 1H, c-Pr); 1.67–1.90(m, 2H, CH$_2$—c-Pr); 2.21(s, 3H, CH$_3$); 2.27(d, J=2 Hz, 3H, CH$_3$); 3.87(s, 3H, OCH$_3$); 4.70(d, J=8.2 Hz, 1H, NH); 4.78–4.83(m, 1H, CH); 6.88(dd J$_1$=12.7 Hz, J$_2$=8.6 Hz, 1H, Ph); 7.05(d, J=2.7 Hz, 1H, Ph); 7.07–7.17(m, 3H, Ph); 7.28(d, J=8.6 Hz, 1H, Ph). |
| VIII.31 | 2-Cl<br>4-OCH$_3$<br>5-CH$_3$ | —CH$_3$ | (1-methyl-2-cyclopropylethyl group attached to phenyl) | 0.06–0.13(m, 2H, c-Pr); 0.40–0.48(m, 2H, c-Pr); 0.60–0.72(m, 1H, c-Pr); 1.63–1.90(m, 2H, CH$_2$—c-Pr); 2.19(s, 6H, CH$_3$); 3.87(s, 3H, OCH$_3$); 4.71(d, J=8.3 Hz, 1H, NH); 4.82–4.90(m, 1H, CH); 6.89(s, 1H, Ph); 7.10(s, 1H, Ph); 7.22–7.41(m, 5H, Ph). |
| VIII.32 | 2-Cl<br>4-Cl<br>H | —CH$_3$ | (1-methyl-2-cyclopropylethyl group attached to phenyl) | 0.07–0.17(m, 2H, c-Pr); 0.40–0.50(m, 2H, c-Pr); 0.63–0.78(m, 1H, c-Pr); 1.65–1.95(m, 2H, CH$_2$—c-Pr); 2.22(s, 3H, CH$_3$); 4.69(d, J=8.2 Hz, 1H, NH): 4.80–4.90(m, 1H, CH); 7.22–7.42(m, 7H, Ph); 7.55(d, J=2.2 Hz, 1H, Ph). |
| VIII.33 | 2-Cl<br>4-OCH$_3$<br>5-CH$_3$ | cyclopropyl | (1-propyl group attached to 4-methylphenyl) | 0.86–0.97(m, 3H, CH$_3$ and 2H, c-Pr); 1.04–1.12(m, 2H, c-Pr); 1.25–1.53(m, 1H, c-Pr and 2H, CH$_2$); 1.68–1.95(m, 2H, CH$_2$); 2.21(s, 3H, CH$_3$); 2.35(s, 3H, CH$_3$); 3.89(s, 3H, OCH$_3$); 4.38(d, J=8.6 Hz, 1H, NH); 4.63–4.73(m, 1H, CH); 6.93(s, 1H, Ph); 7.11–7.30(m, 5H, Ph). |
| VIII.34 | 2-Cl<br>4-Cl<br>H | cyclopropyl | (1-propyl group attached to 4-methylphenyl) | 0.89–1.0(m, 3H, CH$_3$ and 2H, c-Pr); 1.07–1.13(m, 2H, c-Pr); 1.25–1.53(m, 1H, c-Pr and 2H, CH$_2$); 1.68–1.98(m, 2H, CH$_2$); 2.35(s, 3H, CH$_3$); 4.42(d, J=8.5 Hz, 1H, NH); 4.60–4.69(m, 1H, CH); 7.13(d, J=8 Hz, 2H, Ph); 7.25(d, J=8 Hz, 2H, Ph); 7.38(s, 2H, Ph); 7.56(s, 1H, Ph). |
| VIII.35 | 2-Cl<br>4-OCH$_3$<br>H | —CH$_3$ | (1-methyl-2-cyclopropylethyl group attached to 4-fluorophenyl) | 0.06–0.15(m, 2H, c-Pr); 0.40–0.50(m, 2H, c-Pr); 0.60–0.74(m, 1H, c-Pr); 1.65–1.90(m, 2H, CH$_2$—c-Pr); 2.21(s, 3H, CH$_3$); 3.87(s, 3H, OCH$_3$); 4.71(d, J=8.2 Hz, 1H, NH); 4.78–4.85(m, 1H, CH); 6.89(dd J$_1$=2.7 Hz, J$_2$=8.6 Hz, 1H, Ph); 6.98–7.06(m, 3H, Ph); 7.28–7.40(m, 3H, Ph). |

1-[2-Chloro-4-(methylsulphanyl)phenyl]-N-[2-cyclopropyl-1-(3-fluoro-4-methylphenyl)ethyl]-5-methyl-1H-1,2,4-triazol-3-amine Compound VIII.36

470 mg (2.2 mmol) of 2,4-dichlorophenyl-hydrazine hydrochloride are added to a solution of 600 mg (1.9 mmol) of N-acetyl-N'-[2-cyclopropyl-1-(3-fluoro-4-methylphenyl)ethyl]-S-methylisothiourea in 10 ml of dimethylformamide, followed by 800 mg (2.5 mmol) of caesium carbonate and by 4 Å molecular sieve. The reaction mixture is stirred for 4 hours at 140° C. and is then cooled. The molecular sieve is removed by filtration and the filtrate is diluted with 100 ml of ethyl acetate. The organic phase is washed with 1N hydrochloric acid, with water, with a saturated aqueous sodium hydrogencarbonate solution, with water and then with water saturated with sodium chloride. It is dried over sodium sulphate and then the solvents are evaporated under reduced pressure. The crude residue is purified by chromatography on a column of silica gel (eluent: 3/1 (v/v) cyclohexane/ethyl acetate). 385 mg of N-[2-cyclopropyl-1-(3-fluoro-4-methylphenyl)ethyl-1-(2,4-dichlorophenyl)-5-methyl-1H-1,2,4-triazol-3-amine and 115 mg of compound VIII.36 are obtained. Yield 13%.

$^1$H NMR (CDCl$_3$, δ ppm): 0.02–0.13 (m, 2H, c-Pr); 0.40–0.48 (m, 2H, c-Pr); 0.60–0.72 (m, 1H, c-Pr); 1.60–1.88 (m, 2H, CH$_2$-c-Pr); 2.20 (s, 3H, CH$_3$); 2.24 (d, J=1.8 Hz, 3H, CH$_3$); 2.52 (s, 3H, SCH$_3$); 4.75–4.88 (m, 2H, CH and NH); 7.04–7.14 (m, 3H, Ph); 7.18 (dd, J$_1$=2 Hz, J$_2$=8.3 Hz, 1H, Ph); 7.25 (d, J=8.3 Hz, 1H, Ph); 7.33 (d, J=2 Hz, 1H, Ph).

4) Preparation of the Aminotriazoles of Formula (I) by Route B2

EXAMPLE 11

[1-(2-Chloro-4-methoxy-5-methylphenyl)-N-[2-cyclopropyl-1(4-fluorophenyl)ethyl]-5-methyl-N-propyl-1H-1,2,4-triazol-3-amine 240 mg (6 mmol) of potassium hydride (obtained from an oily suspension by washing with pentane and then drying under argon) are suspended in 2 ml of anhydrous benzene. The mixture is stirred at 5–10° C. and 780 mg (1.85 mmol) of compound VIII.1 dissolved in 6 ml of benzene, and 750 mg (2 mmol) of 2,3,11,12-cyclohexano-1,4,7,10,13,16-hexaoxacyclooctadecane are successively added.

After stirring for one hour and thirty minutes at ambient temperature, 0.6 ml (6 mmol) of iodopropane are added and the mixture is stirred for three hours at ambient temperature. The reaction mixture is cooled with an ice bath and 1 ml of ethanol and then 1 ml of water are added, and then it is diluted with 100 ml of ethyl acetate. The organic phase is washed with water and then with water saturated with sodium chloride and dried over sodium sulphate, and then the solvents are evaporated under reduced pressure. The residue is purified by chromatography on a column of silica gel (eluent: 4/1 (v/v) cyclohexane/ethyl acetate). 590 mg of gummy product are obtained. Yield 75%.

$^1$H NMR (CDCl$_3$, δ ppm): 0.1–0.17 (m, 2H, c-Pr); 0.39–0.45 (m, 2H, c-Pr); 0.69–0.76 (m, 4H, CH$_3$ and CH, c-Pr); 1.30–1.45 and 1.50–1.65 (2m, 2H, CH$_2$); 1.88–1.98 (m, 2H, CH$_2$); 2.21 (s, 3H, CH$_3$); 2.22 (s, 3H, CH$_3$); 2.94–3.02 and 3.10–3.20 (2m, 2H, NCH$_2$); 3.87 (s, 3H, CH3); 5.47 (t, 1H, CH); 6.92 (s, 1H, Ph); 6.94–7.02 (m, 2H, Ph); 7.19 (s, 1H, Ph); 7.38–7.44 (m, 2H, Ph).

This product is salified to the hydrochloride; M.p.=38° C. (HCl).

EXAMPLE 12

[1-(2,4-Dichlorophenyl)-N-(2-methoxy-5-methylphenyl)-5-methyl-N-(2-propynyl)-1H-1,2,4-triazol-3-amine 240 mg (6 mmol) of potassium hydride (obtained from an oily suspension by washing with pentane and then drying under argon) are suspended in 2 ml of anhydrous benzene. The mixture is stirred at 10° C. and 730 mg (2 mmol) of compound VIII.3, dissolved in 8 ml of benzene, are added. 75 mg (0.2 mmol) of 2,3,11,12-dicyclohexano-1,4,7,10,13,16-hexaoxacyclo-octadecane are added and the mixture is stirred for two hours at ambient temperature. 0.66 ml (6 mmol) of an 80% solution of propargyl bromide in toluene is subsequently added and the mixture is stirred for one hour at ambient temperature. The reaction mixture is cooled with an ice bath, 1 ml of ethanol and 1 ml of water are then successively added and then the reaction mixture is diluted with 100 ml of ethyl acetate. The organic phase is washed with water and then with water saturated with sodium chloride and dried over sodium sulphate, and then the solvents are evaporated under reduced pressure. The crude extract is purified by chromatography on a column of silica gel (eluent: 3/1 (v/v) cyclohexane/ethyl acetate). 600 mg of product are obtained. Yield 75%.

$^1$H NMR (CDCl$_3$, δ ppm): 2.15 (t, J=2.2 Hz, 1H, CH); 2.21 (s, 3H, CH$_3$); 2.28 (s, 3H, CH$_3$); 3.78 (s, 3H, OCH$_3$); 4.52 (d, J=2.2 Hz, 2H, CH$_2$); 6.84 (d, J=8.3 Hz, 1H, Ph); 7.01 (dd, J$_1$=2 Hz, J$_2$=8.3 Hz, 1H, Ph); 7.23 (d, J=2 Hz, 1H, Ph); 7.29–7.39 (m, 2H, Ph); 7.52 (d, J=2 Hz, 1H, Ph). M.p.=116° C.

EXAMPLES 13 to 53 in the Following TABLE 6 are Synthesized by the Same Method (It Being Possible for Benzene to be Replaced by Tetrahydrofuran)

TABLE 6

Compounds of formula I synthesized by Route B2

(I)

[Structure: 1,2,4-triazole with R4 at 5-position, N(R5)(R6) at 3-position, and N1-substituted phenyl bearing R1 (ortho), R2 (para), R3 (meta)]

| Example | R₁, R₂, R₃ | R₄ | R₅ | R₆ | Salt; M.p. (° C.) |
|---|---|---|---|---|---|
| 13 | 2-Cl<br>4-OCH₃<br>5-CH₃ | —CH₃ | —CH₂—C≡CH | 1-(4-fluorophenyl)-2-cyclopropyl-ethyl (via CH(CH₃)CH₂-cyclopropyl with 4-F-phenyl) | HCl; 72 |
| 14 | 2-Cl<br>4-OCH₃<br>5-CH₃ | cyclopropyl | —(CH₂)₂CH₃ | 1-(4-fluorophenyl)-2-cyclopropyl-ethyl | HCl; 121 |
| 15 | 2-Cl<br>4-OCH₃<br>5-CH₃ | cyclopropyl | —CH₂—C≡CH | 1-(4-fluorophenyl)-2-cyclopropyl-ethyl | HCl; 139 |
| 16 | 2-Cl<br>4-Cl<br>H | —CH₃ | —(CH₂)₂CH₃ | 2-methoxy-5-methylphenyl (2,4-dimethyl-methoxyphenyl group) | HCl; 149 |
| 17 | 2-Cl<br>4-OCH₃<br>5-CH₃ | cyclopropyl | —(CH₂)₃CH₃ | 1-(4-fluorophenyl)-2-cyclopropyl-ethyl | HCl; 91 |
| 18 | 2-Cl<br>4-CF₃<br>6-Cl | cyclopropyl | —(CH₂)₂CH₃ | 1-(4-fluorophenyl)-2-cyclopropyl-ethyl | HBr; 90 |

TABLE 6-continued
Compounds of formula I synthesized by Route B2
(I)
| Example | R₁, R₂, R₃ | R₄ | R₅ | R₆ | Salt; M.p. (° C.) |
|---|---|---|---|---|---|
| 19 | 2-Cl<br>4-Cl<br>H | 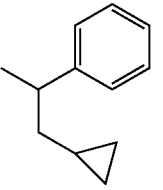 | —(CH₂)₂CH₃ |  | HCl; 132 |
| 20 | 2-Cl<br>4-OCH₃<br>5-CH₃ | 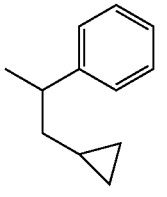 | —(CH₂)₂CH₃ |  | 0.75 HCl; 98 |
| 21 | 2-Cl<br>4-OCH₃<br>5-CH₃ | 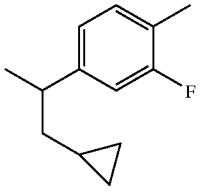 | —(CH₂)₂CH₃ |  | 0.75 HCl; 88 |
| 22 | 2-Cl<br>4-OCH₃<br>5-CH₃ | 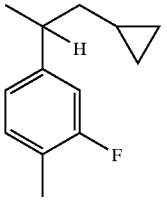 | —(CH₂)₂CH₃ |  | 0.75 HCl; 90<br>[α]²⁰_D = −105°<br>(c = 0.52 MeOH) |
| 23 | 2-Cl<br>4-OCH₃<br>5-CH₃ | 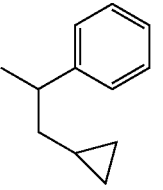 | —CH₂—C≡CH |  | HCl; 129 |
| 24 | 2-Cl<br>4-OCH₃<br>5-CH₃ | | —(CH₂)₂CH₃ | 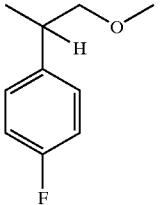 | HCl; 132<br>[α]²⁰_D = −71°<br>(c = 0.52 MeOH) |

TABLE 6-continued

Compounds of formula I synthesized by Route B2

(I)

| Example | R₁, R₂, R₃ | R₄ | R₅ | R₆ | Salt; M.p. (° C.) |
|---|---|---|---|---|---|
| 25 | 2-Cl<br>4-OCH₃<br>5-CH₃ | cyclopropyl | —CH₂—C≡CH | 1-(3-fluoro-4-methylphenyl)-2-cyclopropylethyl | HBr; 99<br>$[\alpha]^{20}_D = -94°$<br>(c = 0.25 CH₂Cl₂) |
| 26 | 2-Cl<br>4-Cl<br>H | cyclopropyl | —(CH₂)₂CH₃ | 1-(3-fluoro-4-methylphenyl)-2-cyclopropylethyl | HCl; 139 |
| 27 | 2-Cl<br>4-Cl<br>H | cyclopropyl | —(CH₂)₂CH₃ | 1-(4-fluorophenyl)-2-methoxyethyl | HCl; 119<br>$[\alpha]^{20}_D = -75°$<br>(c = 0.73 MeOH) |
| 28 | 2-CH₃<br>4-CH₃<br>H | cyclopropyl | —(CH₂)₂CH₃ | 1-(3-fluoro-4-methylphenyl)-2-cyclopropylethyl | HCl; 77<br>$[\alpha]^{20}_D = -105°$<br>(c = 0.55 MeOH) |
| 29 | 2-Cl<br>4-Cl<br>H | —CH₂CH₃ | —(CH₂)₂CH₃ | 1-phenylbutyl | HCl; 130<br>$[\alpha]^{20}_D = -116°$<br>(c = 0.7 CH₂Cl₂) |
| 30 | 2-Cl<br>4-OCH₃<br>5-CH₃ | —CH₃ | —(CH₂)₂CH₃ | 1-phenylbutyl | HCl; 87<br>$[\alpha]^{20}_D = -114°$<br>(c = 0.55 CH₂Cl₂) |

TABLE 6-continued

Compounds of formula I synthesized by Route B2

(I)

| Example | R₁, R₂, R₃ | R₄ | R₅ | R₆ | Salt; M.p. (° C.) |
|---|---|---|---|---|---|
| 31 | 2-Cl<br>4-OCH₃<br>5-CH₃ | —CH₃ | —(CH₂)₂CH₃ | 1-(3-fluoro-4-methylphenyl)-2-cyclopropylethyl | HCl; 114<br>$[\alpha]^{20}_D = -103°$<br>(c = 0.71 CH₂Cl₂) |
| 32 | 2-Cl<br>4-Cl<br>H | —CH₃ | —(CH₂)₂CH₃ | 1-(4-fluorophenyl)-2-cyclopropylethyl | HCl; 82<br>$[\alpha]^{20}_D = -89°$<br>(c = 0.5 CH₂Cl₂) |
| 33 | 2-Cl<br>4-OCH₃<br>5-CH₃ | —CH₂CH₃ | —(CH₂)₂CH₃ | 1-(3-fluoro-4-methylphenyl)-2-cyclopropylethyl | HCl; 93<br>$[\alpha]^{20}_D = -96°$<br>(c = 0.5 CH₂Cl₂) |
| 34 | 2-Cl<br>4-Cl<br>H | —CH₂CH₃ | —(CH₂)₂CH₃ | 1-(4-fluorophenyl)-2-cyclopropylethyl | HCl; 139<br>$[\alpha]^{20}_D = -88°$<br>(c = 0.5 CH₂Cl₂) |
| 35 | 2-Cl<br>4-OCH₃<br>5-CH₃ | —CH₃ | —CH₂—C≡CH | 1-(3-fluoro-4-methylphenyl)-2-cyclopropylethyl | HCl; 89<br>$[\alpha]^{20}_D = -98°$<br>(c = 0.47 CH₂Cl₂) |
| 36 | 2-Cl<br>4-Cl<br>H | cyclopropyl | —(CH₂)₃CH₃ | 1-phenylbutyl | HCl; 98<br>$[\alpha]^{20}_D = -72°$<br>(c = 0.52 CH₂Cl₂) |

TABLE 6-continued

Compounds of formula I synthesized by Route B2

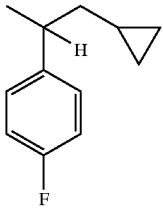

(I)

| Example | R₁, R₂, R₃ | R₄ | R₅ | R₆ | Salt; M.p. (° C.) |
|---|---|---|---|---|---|
| 37 | 2-Cl<br>4-OCH₃<br>5-CH₃ | —CH₂CH₃ | —(CH₂)₂CH₃ | 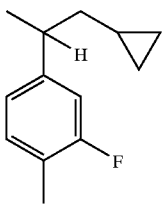 | HCl; 79<br>$[\alpha]^{20}_D = -73°$<br>(c = 0.9 CH₂Cl₂) |
| 38 | 2-Cl<br>4-Cl<br>H | —CH₃ | —(CH₂)₂CH₃ | 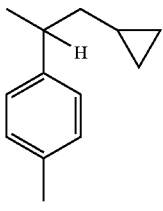 | HCl; 93<br>$[\alpha]^{20}_D = -99°$<br>(c = 0.52 CH₂Cl₂) |
| 39 | 2-Cl<br>4-OCH₃<br>5-CH₃ | —CH₃ | —(CH₂)₂CH₃ | 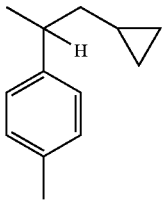 | HCl; 139<br>$[\alpha]^{20}_D = -103°$<br>(c = 0.56 CH₂Cl₂) |
| 40 | 2-Cl<br>4-Cl<br>H | —CH₃ | —(CH₂)₂CH₃ |  | HCl; 94<br>$[\alpha]^{20}_D = -99°$<br>(c = 0.5 CH₂Cl₂) |
| 41 | 2-Cl<br>4-OCH₃<br>5-CH₃ | 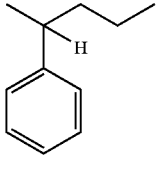 | —(CH₂)₂CH₃ | 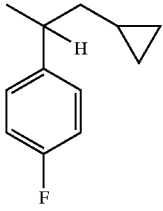 | HCl; 65<br>$[\alpha]^{20}_D = -116°$<br>(c = 0.7 CH₂Cl₂) |
| 42 | 2-Cl<br>4-OCH₃<br>5-CH₃ | —CH₃ | —(CH₂)₂CH₃ |  | HCl; 120<br>$[\alpha]^{20}_D = -138°$<br>(c = 0.33 CH₂Cl₂) |

TABLE 6-continued

Compounds of formula I synthesized by Route B2

(I)

| Example | R₁, R₂, R₃ | R₄ | R₅ | R₆ | Salt; M.p. (° C.) |
|---|---|---|---|---|---|
| 43 | 2-Cl<br>4-CF₃<br>H | —CH₃ | —(CH₂)₂CH₃ | (cyclopropylmethyl-CH(CH₃)-(3-fluoro-4-methylphenyl)) | HCl; 138<br>$[\alpha]^{20}_D = -92°$<br>(c = 0.62 CH₂Cl₂) |
| 44 | 2-Cl<br>4-OCH₃<br>5-CH₃ | —CH₃ | —(CH₂)₂CH₃ | (cyclopropylmethyl-CH(CH₃)-(benzo[1,3]dioxol-5-yl)) | HCl; 98<br>$[\alpha]^{20}_D = -102°$<br>(c = 0.64 CH₂Cl₂) |
| 45 | 2-Cl<br>4-Cl<br>H | —CH₃ | —(CH₂)₂CH₃ | (cyclopropylmethyl-CH(CH₃)-(benzo[1,3]dioxol-5-yl)) | HCl; 76<br>$[\alpha]^{20}_D = -131°$<br>(c = 0.35 CH₂Cl₂) |
| 46 | 2-Cl<br>4-OCH₃<br>5-CH₃ | —CH₃ | —(CH₂)₂CH₃ | (cyclopropylmethyl-CH(CH₃)-(4-methoxymethylphenyl)) | HCl; 143<br>$[\alpha]^{20}_D = -97°$<br>(c = 0.28 CH₂Cl₂) |
| 47 | 2-Cl<br>4-OCH₃<br>H | —CH₃ | —(CH₂)₂CH₃ | (cyclopropylmethyl-CH(CH₃)-(3-fluoro-4-methylphenyl)) | HCl; 118<br>$[\alpha]^{20}_D = -100°$<br>(c = 0.37 CH₂Cl₂) |

TABLE 6-continued

Compounds of formula I synthesized by Route B2

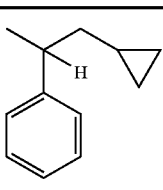
(I)

| Example | R₁, R₂, R₃ | R₄ | R₅ | R₆ | Salt; M.p. (° C.) |
|---------|------------|------|--------------|--------------|-------------------|
| 48 | 2-Cl<br>4-OCH₃<br>5-CH₃ | —CH₃ | —(CH₂)₂CH₃ | 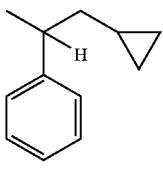 | HCl; 89<br>$[\alpha]^{20}_D = -95°$<br>(c = 0.38 CH₂Cl₂) |
| 49 | 2-Cl<br>4-Cl<br>H | —CH₃ | —(CH₂)₂CH₃ |  | HCl; 113<br>$[\alpha]^{20}_D = -107°$<br>(c = 0.36 CH₂Cl₂) |
| 50 | 2-Cl<br>4-OCH₃<br>5-CH₃ | 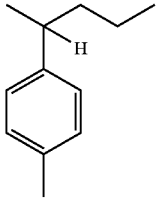 | —(CH₂)₂CH₃ |  | HCl; 78<br>$[\alpha]^{20}_D = -123°$<br>(c = 0.52 CH₂Cl₂) |
| 51 | 2-Cl<br>4-Cl<br>H | 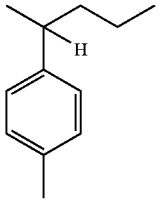 | —(CH₂)₂CH₃ | | HCl; 85<br>$[\alpha]^{20}_D = -122°$<br>(c = 0.32 CH₂Cl₂) |
| 52 | 2-Cl<br>4-SMe<br>H | —CH₃ | —(CH₂)₂CH₃ | 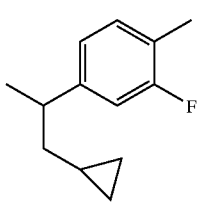 | HCl; 73 |
| 53 | 2-Cl<br>4-OCH₃<br>H | —CH₃ | —(CH₂)₂CH₃ | 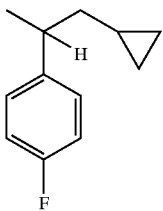 | HCl; 83<br>$[\alpha]^{20}_D = -101°$<br>(c = 0.32 CH₂Cl₂) |

What is claimed is:

1. A compound of formula:

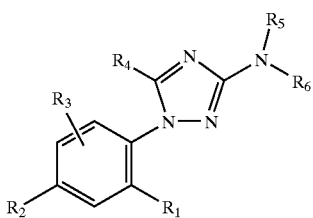

in which:
- $R_1$ and $R_2$ represent, each independently of the other, a halogen atom; a $(C_1–C_5)$alkyl; a $(C_1–C_5)$alkoxy; a nitro, trifluoromethyl or cyano group; an $NR_aR_b$ amino group in which $R_a$ and $R_b$ represent, each independently of the other, a hydrogen, a $(C_1–C_3)$alkyl or a $CO(C_1–C_3)$alkyl; or an S—R group in which R represents a hydrogen atom or a $(C_1–C_5)$alkyl, it being possible for the sulphur atom to be monooxidized or dioxidized;
- $R_3$ represents hydrogen or is as defined above for $R_1$;
- $R_4$ represents hydrogen; a halogen; a $(C_1–C_5)$alkyl; a $(C_3–C_5)$cycloalkyl; a $(C_3–C_5)$cycloalkyl$(C_1–C_2)$alkyl; or an $R_c$—X—$(C_1–C_2)$alkyl group in which $R_c$ represents hydrogen or a $(C_1–C_3)$alkyl and X represents O, S, SO or $SO_2$;
- $R_5$ represents a $(C_1–C_5)$alkyl, an alkynyl with 3 to 5 carbon atoms or an alkenyl with 3 to 5 carbon atoms; a $(C_3–C_5)$cycloalkyl$(C_1–C_3)$alkyl; or a $(C_1–C_3)$alkyl-X—$(C_0–C_3)$alkyl in which X represents O, S, SO or $SO_2$;
- $R_6$ represents a —$CHR_7R_8$, in which
- $R_7$ represents a phenyl group which can be substituted in the 3-, 4- and 5-positions by one or more Z' radicals, with Z' representing a halogen; a nitro, trifluoromethyl or cyano group; a $(C_1–C_5)$alkyl; a $(C_1–C_5)$alkyl-X— or $(C_1–C_3)$alkyl-X—$(C_1–C_2)$alkyl where X represents O, S, SO or $SO_2$; a hydroxy$(C_1–C_3)$alkyl; a $COR_d$ or $COOR_d$ in which $R_d$ is as defined above; a methylenedioxy or an ethylenedioxy;
- $R_8$ represents a $(C_3–C_5)$cycloalkyl$(C_1–C_3)$alkyl; or a pharmaceutically acceptable addition salt, hydrate and/or solvate thereof.

2. A compound according to claim 1, in which:
- $R_1$ and $R_2$ represent, each independently of the other, a halogen atom; a $(C_1–C_5)$alkyl; a $(C_1–C_5)$alkoxy; a trifluoromethyl or an S—R group in which R represents a $(C_1–C_5)$alkyl;
- $R_3$ represents hydrogen or a $(C_1–C_5)$alkyl;
- $R_4$ represents a $(C_1–C_5)$alkyl; a $(C_3–C_5)$cycloalkyl or an $R_a$—X—$(C_1–C_2)$alkyl group in which $R_a$ represents a $(C_1–C_3)$alkyl and X represents O;
- $R_5$ represents a $(C_1–C_5)$alkyl or an alkynyl with 3 to 5 carbon atoms;
- $R_6$ represents —$CHR_7R_8$, in which
- $R_7$ represents a phenyl group which can be substituted in the 3-, 4- and 5-positions by one or more Z' radicals, with Z' representing a halogen; a $(C_1–C_5)$alkyl; a $(C_1–C_5)$alkyl-X— or $(C_1–C_3)$alkyl-X—$(C_1–C_2)$alkyl where X represents O; or a methylenedioxy group;
- $R_8$ represents a $(C_3–C_5)$cycloalkyl$(C_1–C_3)$alkyl; or a pharmaceutically acceptable addition salt, hydrate and/or solvate thereof.

3. A compound according to claim 1 in which $R_5$ represents a propyl or propargyl group.

4. A compound according to claim 1 in the enantiomeric form.

5. A compound according to claim 1 chosen from:
- 5-Cyclopropyl-N-[2-cyclopropyl-1-(4-fluorophenyl)ethyl]-1-(2,4-dichlorophenyl)-N-propyl-1H-1,2,4-triazol-3-amine hydrochloride
- N-[2-Cyclopropyl-1-(4-fluorophenyl)ethyl]-1-(2,4-dichlorophenyl)-5-(methoxymethyl)-N-propyl-1H-1,2,4-triazol-3-amine hydrochloride
- N-[2Cyclopropyl-1-(4-fluorophenyl)ethyl]-1-[2,6-dichloro-4-(trifluoromethyl)phenyl]-5-methyl-N-propyl-1H-1,2,4-triazol-3-amine hydrochloride
- 1-(2-Chloro-4-methoxy-5-methylphenyl)-N-[2-cyclopropyl-1-(4-fluorophenyl)ethyl]-5-methyl-N-(2-propynyl)-1H-1,2,4-triazol-3-amine hydrochloride
- 1-(2-Chloro-4-methoxy-5-methylphenyl)-N-[2-cyclopropyl-1-(4-fluorophenyl)ethyl]-5-methyl-N-propyl-1H-1,2,4-triazol-3-amine hydrochloride
- 1-(2-Chloro-4-methoxy-5-methylphenyl)-5-cyclopropyl-N-[2-cyclopropyl-1-(4-fluorophenyl)ethyl]-N-(2-propynyl)-1H-1,2,4-triazol-3-amine hydrochloride
- 5-Cyclopropyl-N-[2-cyclopropyl-1-(4-fluorophenyl)ethyl]-1-[2,6-dichloro-4-(trifluoromethyl)phenyl]-N-propyl-1H-1,2,4-triazol-3-amine hydrobromide
- 5-Cyclopropyl-N-(2-cyclopropyl-1-phenylethyl)-1-(2,4-dichlorophenyl)-N-propyl-1H-1,2,4-triazol-3-amine hydrochloride
- 1-(2-Chloro-4-methoxy-5-methylphenyl)-5-cyclopropyl-N-(2cyclopropyl-1-phenylethyl)-N-propyl-1H-1,2,4-triazol-3-amine hydrochloride
- 1-(2-Chloro-4-methoxy-5-methylphenyl)-5-cyclopropyl-N-[(1S)-2-cyclopropyl-1-(3-fluoro-4-methylphenyl)-ethyl]-N-propyl-1H-1,2,4-triazol-3-amine hydrochloride
- 1-(2-Chloro-4-methoxy-5-methylphenyl)-5-cyclopropyl-N-(2-cyclopropyl-1-phenylethyl)-N-(2-propynyl)-1H-1,2,4-triazol-3-amine hydrochloride
- 1-(2-Chloro-4-methoxy-5-methylphenyl)-5-cyclopropyl-N-[(1S)-2-cyclopropyl-1-(3-fluoro-4-methylphenyl)ethyl]-N-(2-propynyl)-1H-1,2,4-triazol-3-amine hydrobromide
- 5-Cyclopropyl-N-[2-cyclopropyl-1-(3-fluoro-4-methylphenyl)ethyl]-1-(2,4-dichlorophenyl)-N-propyl-1H-1,2,4-triazol-3-amine hydrochloride
- 5-Cyclopropyl-N-[(1S)-2-cyclopropyl-1-(3-fluoro-4-methylphenyl)ethyl]-1-(2,4-dimethylphenyl)-N-propyl-1H-1,2,4-triazol-3-amine hydrochloride
- 1-(2-Chloro-4-methoxy-5-methylphenyl)-N-[(1S)-2cyclopropyl-1-(3-fluoro-4-methylphenyl)ethyl]-5-methyl-N-propyl-1H-1,2,4-triazol-3-amine hydrochloride
- N-[(1S)-2-Cyclopropyl-1-(4-fluorophenyl)ethyl]-1-(2,4-dichlorophenyl)-5-methyl-N-propyl-1H-1,2,4-triazol-3-amine hydrochloride
- 1-(2-Chloro-4-methoxy-5-methylphenyl)-N-[(1S)-2-cyclopropyl-1-(3-fluoro-4-methylphenyl)ethyl]-5-ethyl-N-propyl-1H-1,2,4-triazol-3-amine hydrochloride
- N-(1S)-2-Cyclopropyl-1-(4-fluorophenyl)ethyl]-1-(2,4-dichlorophenyl)-5-ethyl-N-propyl-1H-1,2,4-triazol-3-amine hydrochloride
- 1-(2-Chloro-4-methoxy-5-methylphenyl)-N-[(1S)-2-cyclopropyl-1-(3-fluoro-4-methylphenyl)ethyl]-5-methyl-N-(2-propynyl)-1H-1,2,4-triazol-3-amine hydrochloride 1-(2-Chloro-4methoxy-5-methylphenyl)-N-[(1S)-2-cyclopropyl-1-(4-fluorophenyl)ethyl]-5-ethyl-N-propyl-1H-1,2,4-triazol-3-amine hydrochloride N-[(1S)-2-Cyclopropyl-1-(3-fluoro-4-methylphenyl)ethyl]-1-(2,4-dichlorophenyl)-5-methyl-N-propyl-1H-1,2,4-triazol-3-amine hydrochloride 1-(2-Chloro-4-methoxy-5-methylphenyl)-N-[(1S)-2-cyclopropyl-1-(4-methylphenyl)ethyl[-5-methyl-N-propyl-1H-1,2,4-triazol-3-amine hydrochloride N-[(1S)-2-Cyclopropyl-1-(4-methylphenyl)ethyl]-1-(2,4-dichlorophenyl)-5-methyl-N-propyl-1H-1,2,4-triazol-3-amine hydrochloride 1(2-Chloro-4-methoxy-5-methylphenyl)-N-[(1S)-2-cyclopropyl-1-(4-fluorophenyl)ethyl]-5-methyl-N-propyl-1H-1,2,4-triazol-3-amine hydrochloride 1-[2-Chloro-4-(trifluoromethyl)phenyl]-N-[(1S)-2-cyclopropyl-1-(3-fluoro-4-methylphenyl)ethyl]-5-methyl-N-propyl-1H-1,2,4-triazol-3-amine hydrochloride N-[(1S)-1-(1,3-Benzodioxol-5-yl)-2-cyclopropylethyl]-1-(2-chloro-4-methoxy-5-methylphenyl)-5-methyl-N-propyl-1H-1,2,4-triazol-3-amine hydrochloride N-[(1S)-1-(1,3-Benzodioxol-5-yl)-2-cyclopropylethyl]-1-(2,4-dichlorophenyl)-5-methyl-N-propyl-1H-1,2,4-triazol-3-amine hydrochloride 1-(2-Chloro-4-methoxy-5-methylphenyl)-N-{(1S)-2-cyclopropyl-1-[(4-methoxymethyl)phenyl]ethyl}-5-methyl-N-propyl-1H-1,2,4-triazol-3-amine hydrochloride 1-(2-Chloro-4-methoxyphenyl)-N-[(1S)-2-cyclopropyl-1-(3-fluoro-4-methylphenyl)ethyl]-5-methyl-N-propyl-1H-1,2,4-triazol-3-amine hydrochloride 1-(2-Chloro-4-methoxy-5-methylphenyl)-N-[(1S)-2-cyclopropyl-1-phenyl)ethyl]-5-methyl-N-propyl-1H-1,2,4-triazol-3-amine hydrochloride N-[(1S)-2-Cyclopropyl-1-phenyl)ethyl]-1-(2,4-dichlorophenyl)-5-methyl-N-propyl-1H-1,2,4-triazol-3-amine hydrochloride 1-[2Chloro-4-(methylsulphanyl)phenyl]-N-[2-cyclopropyl-1-(3-fluoro-4-methylphenyl)ethyl]-5-methyl-N-propyl-1H-1,2,4-triazol-3-amine hydrochloride 1-(2-Chloro-4-methoxyphenyl)-N-[(1S)-2-cyclopropyl-1-(4-fluorophenyl)ethyl]-5-methyl-N-propyl-1H-1,2,4-triazol-3-amine hydrochloride or a corresponding base, other pharmaceutically acceptable addition salt, solvate and/or hydrate thereof.

6. A pharmaceutical composition which comprises, as active principle, a compound according to claim 1 in combination with one or more appropriate excipients.

7. A compound according to claim 2 in which $R_5$ represents a propyl or propargyl group.

8. A compound according to claim 2 in the enantiomeric form.

9. A compound according to claim 3 in the enantiomeric form.

10. A pharmaceutical composition which comprises, as active principle, a compound according to claim 2 in combination with one or more appropriate excipients.

11. A pharmaceutical composition which comprises, as active principle, a compound according to claim 3 in combination with one or more appropriate excipients.

12. A pharmaceutical composition which comprises, as active principle, a compound according to claim 4 in combination with one or more appropriate excipients.

13. A pharmaceutical composition which comprises, as active principle, a compound according to claim 5 in combination with one or more appropriate excipients.

14. A pharmaceutical composition which comprises, as active principle, a compound according to claim 7 in combination with one or more appropriate excipients.

15. A pharmaceutical composition which comprises, as active principle, a compound according to claim 8 in combination with one or more appropriate excipients.

16. A pharmaceutical composition which comprises, as active principle, a compound according to claim 9 in combination with one or more appropriate excipients.

17. 1-(2-Chloro-4-methoxy-5-methylphenyl)-N-[(1S)-2-cyclopropyl-1-(3-fluoro-4-methylphenyl)ethyl]-5-methyl-N-propyl-1H-1,2,4-triazol-3-amine hydrochloride, or a corresponding base, other pharmaceutically acceptable addition salt, solvate and/or hydrate thereof according to claim 5.

18. 1-(2-Chloro-4-methoxy-5-methylphenyl)-N-[(1S)-2-cyclopropyl-1-(3-fluoro-4-methylphenyl)ethyl]-5-methyl-N-propyl-1H-1,2,4-triazol-3-amine hydrochloride according to claim 17.

19. A pharmaceutical composition which comprises, as active principle, a compound according to claim 17 in combination with one or more appropriate excipients.

20. A pharmaceutical composition which comprises, as active principle, a compound according to claim 18 in combination with one or more appropriate excipients.

* * * * *

UNITED STATES PATENT AND TRADEMARK OFFICE
CERTIFICATE OF CORRECTION

PATENT NO.        : 6,806,282 B2                                              Page 1 of 1
APPLICATION NO. : 10/149499
DATED             : October 19, 2004
INVENTOR(S)       : Geslin et al.

It is certified that error appears in the above-identified patent and that said Letters Patent is hereby corrected as shown below:

Column 2, line 54:      "rCFR" should read as -- CRF --.

Column 37, line 61:     "Compound VIIX.1" should read as -- Compound VIII.1 --.

Column 50, line 6 of the NMR data for Compound No. VIII.30: "6.88(dd $J_1$=12.7 Hz" should read as -- 6.88(dd $J_1$=2.7 Hz --.

Column 68, line 30:     "2cyclopropyl" should read as -- 2-cyclopropyl --.

Column 68, line 51:     "2cyclopropyl" should read as -- 2-cyclopropyl --.

Column 69, line 1:      "4methoxy" should read as -- 4-methoxy --.

Column 69, line 13:     "1(2-Chloro" should read as -- 1-(2-Chloro --.

Column 69, line 39:     "2Chloro" should read as -- 2-Chloro --.

Signed and Sealed this

Eighteenth Day of May, 2010

David J. Kappos
*Director of the United States Patent and Trademark Office*